(12) United States Patent
Sanford et al.

(10) Patent No.: US 11,056,705 B2
(45) Date of Patent: Jul. 6, 2021

(54) ORGANIC ANOLYTE MATERIALS FOR FLOW BATTERIES

(71) Applicants: THE REGENTS OF THE UNIVERSITY OF MICHIGAN, Ann Arbor, MI (US); THE BOARD OF TRUSTEES OF THE UNIVERSITY OF ILLINOIS, Urbana, IL (US)

(72) Inventors: Melanie S. Sanford, Ann Arbor, MI (US); Christo Slavov Sevov, Ann Arbor, MI (US); Rachel Brooner, Midland, MI (US); Etienne Chénard, Urbana, IL (US)

(73) Assignees: THE REGENTS OF THE UNIVERSITY OF MICHIGAN, Ann Arbor, MI (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 457 days.

(21) Appl. No.: 15/580,048

(22) PCT Filed: Jun. 8, 2016

(86) PCT No.: PCT/US2016/036336
§ 371 (c)(1),
(2) Date: Dec. 6, 2017

(87) PCT Pub. No.: WO2016/200870
PCT Pub. Date: Dec. 15, 2016

(65) Prior Publication Data
US 2018/0138539 A1    May 17, 2018

Related U.S. Application Data

(60) Provisional application No. 62/221,796, filed on Sep. 22, 2015, provisional application No. 62/172,508, filed on Jun. 8, 2015.

(51) Int. Cl.
*H01M 8/18* (2006.01)
*C07D 213/55* (2006.01)
(Continued)

(52) U.S. Cl.
CPC .......... *H01M 8/188* (2013.01); *C07D 213/51* (2013.01); *C07D 213/55* (2013.01);
(Continued)

(58) Field of Classification Search
CPC combination set(s) only.
See application file for complete search history.

(56) References Cited

U.S. PATENT DOCUMENTS

2002/0025477 A1    2/2002   Itagaki et al.
2005/0075894 A1    4/2005   Bushey et al.
(Continued)

FOREIGN PATENT DOCUMENTS

EP    1385182    *    1/2004

OTHER PUBLICATIONS

International Search Report in PCT/US2010/036336, dated Oct. 26, 2016.

*Primary Examiner* — Christopher P Domone
(74) *Attorney, Agent, or Firm* — Marshall, Gerstein & Borun LLP

(57) ABSTRACT

Organic anolyte materials for redox flow batteries and redox flow batteries containing organic anolyte materials are disclosed.

19 Claims, 13 Drawing Sheets

(51) Int. Cl.
*C07D 213/89*  (2006.01)
*C07F 5/02*  (2006.01)
*H01M 4/36*  (2006.01)
*H01M 10/0569*  (2010.01)
*H01M 10/0567*  (2010.01)
*H01M 2/14*  (2006.01)
*C07D 213/56*  (2006.01)
*C07D 213/51*  (2006.01)
*H01M 4/90*  (2006.01)
*H01M 50/40*  (2021.01)

(52) U.S. Cl.
CPC .......... *C07D 213/56* (2013.01); *C07D 213/89* (2013.01); *C07F 5/022* (2013.01); *H01M 4/368* (2013.01); *H01M 4/9008* (2013.01); *H01M 10/0567* (2013.01); *H01M 10/0569* (2013.01); *H01M 50/40* (2021.01); *H01M 2300/0028* (2013.01); *Y02E 60/50* (2013.01)

(56) References Cited

U.S. PATENT DOCUMENTS

| | | |
|---|---|---|
| 2013/0224538 A1 | 8/2013 | Jansen et al. |
| 2015/0125729 A1* | 5/2015 | Lee .................... H01M 8/1023 429/105 |

* cited by examiner

R₂ = 4-OMe, 4-Me, 4-Cl, 4-H, 2-Me, 2,4,6-trimethyl, 2,6-dimethyl
R₁ = Me, Et, iPr, $^t$Bu, Ad (adamantyl)
X = OTs, OTf, Br, Cl, I, BF₄, PF₆

R₂ = 4-OMe, 4-Me, 4-Cl, 4-H, 2-Me, 2,4,6-trimethyl, 2,6-dimethyl
R₁ = 4-OMe, 4-Me, 4-Cl, 4-H, 2-Me, 2,4,6-trimethyl, 2,6-dimethyl
X = OTs, OTf, Br, Cl, I, BF₄, PF₆

R₂ = Me, Et, iPr, $^t$Bu, Ad (adamantyl), CF₃

R₁ = 4-OMe, 4-Me, 4-Cl, 4-H, 2-Me, 2,4,6-trimethyl, 2,6-dimethyl
X = OTs, OTf, Br, Cl, I, BF₄, PF₆

US 11,056,705 B2

ORGANIC ANOLYTE MATERIALS FOR FLOW BATTERIES

CROSS-REFERENCE TO RELATED APPLICATIONS

This application is the U.S. National Stage application of International Patent Application No. PCT/US2016/036336, filed Jun. 8, 2016, which claims the benefit of U.S. Provisional Patent Application No. 62/172,508, filed Jun. 8, 2015 and U.S. Provisional Patent Application No. 62/221,796, filed Sep. 22, 2015, each incorporated herein by reference in its entirety.

STATEMENT OF GOVERNMENT RIGHTS

This invention was made with government support under grant number DE-FA 0000559 awarded by the U.S. Department of Energy. The government has certain rights in the invention.

BACKGROUND

Field of the Invention

The present invention generally relates to organic anolyte materials for redox flow batteries and to redox flow batteries containing organic anolyte materials.

BRIEF DESCRIPTION OF RELATED TECHNOLOGY

Electrical energy is currently the single largest form of energy consumed worldwide. Furthermore, the consumption of electricity is predicted to double by 2050. It is widely accepted that increasing global demands should be met with energy sources that do not contribute to the accumulation of greenhouse gases or to the exhaustion of the limited supply of fossil fuels. To address this challenge, major effort is focused on the development of technologies that convert renewables into electrical energy. However, the integration of renewables into the electrical grid remains limited due to the variable and intermittent nature of energy sources like solar and wind. Energy storage systems (EESs) that can respond rapidly to changes in flux from renewable sources could allow for the large-scale penetration of these energy sources into the electric grid.

Electrochemical energy storage is currently dominated by Li-ion batteries, which operate by intercalation of Li-ions into a graphite electrode. Advances in the intercalation supports have incrementally increased the capacity of Li-ion batteries by 8% per year and reduced their cost by 5% per year. This progress has slowly revolutionized portable technologies and, more recently, has begun shifting the paradigm of batteries for transportation applications. However, the use of Li-ion technologies in stationary, grid-scale storage applications remains cost-prohibitive. Moreover, the slow year-to-year increases in capacity and decreases in cost have motivated research into alternative storage systems that allow for more transformative changes.

Redox-flow batteries (RFBs) represent a promising technology for grid-scale energy storage. In RFBs, solutions of anolyte and catholyte materials undergo electrochemical reactions as they are passed over a current collector. As a result, the capacity and power can be scaled independently, which dramatically reduces cost. Capacity can be increased by increasing the volume of the electroactive solution, while power can be increased by expanding the surface area of the current collector. These features mitigate mechanical fatigue, which is common in competing battery technologies that involve deposition and dissolution of electroactive materials at electrode surfaces. In addition, the physical separation of the electroactive materials in RFBs precludes exotherms that can result from mixing, providing a valuable safety feature for large-scale applications.

SUMMARY

The present disclosure is directed to an anolyte material for a redox flow battery and to a redox flow battery comprising an anolyte material as disclosed herein.

In one aspect, the disclosure provides an anolyte solution comprising a non-aqueous solvent, a supporting electrolyte, and a compound of formula I as an anolyte material:

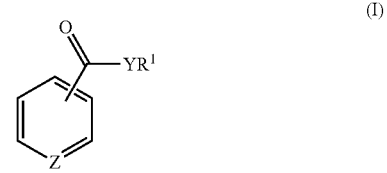

(I)

wherein Y is selected from the group consisting of null, O, and $NR^3$; Z is selected from the group consisting of N, $N^+O^-$, $N^+R^-$, and

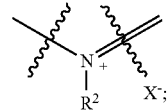

$R^1$ is selected from the group consisting of optionally substituted $C_{1-10}$ alkyl, $C_{3-12}$ cycloalkyl, and optionally substituted phenyl; $R^2$ is selected from the group consisting of optionally substituted $C_{1-10}$ alkyl, $C_{3-12}$ cycloalkyl, and optionally substituted phenyl; $R^3$ is an optionally substituted $C_{1-10}$ alkyl; R is a Lewis acid; and $X^-$ is an anion.

In another aspect, the disclosure provides a redox flow battery comprising an anolyte solution as disclosed herein.

These and other embodiments and features of the present invention will become apparent from the following detailed description of the preferred embodiments.

BRIEF DESCRIPTION OF THE DRAWINGS

FIG. 11a is a scheme showing synthesis of Na-10a$^{(-)}$ by chemical reduction of 10a. FIG. 11b is a $^1$H NMR spectrum of 10a and labeled resonances. FIG. 11c is a $^1$H NMR spectrum of Na-10a$^{(-)}$ and labeled resonances.

DETAILED DESCRIPTION

Figure 1:
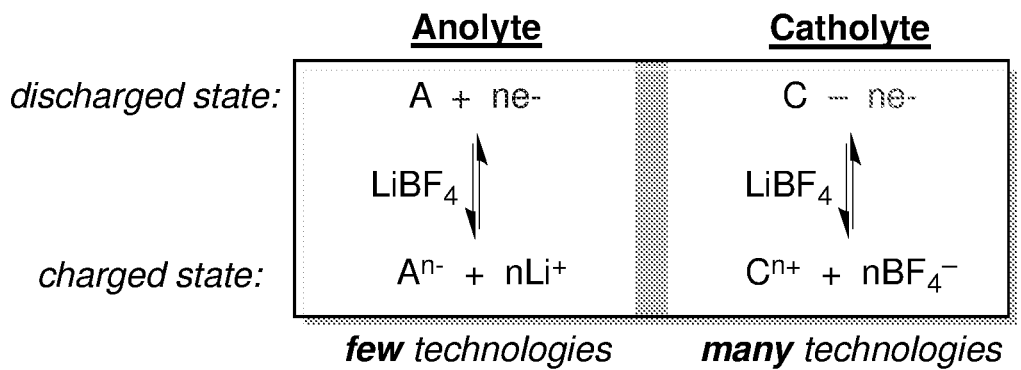
FIG. 1 is a schematic drawing showing half-cell reactions of anolyte and catholyte materials in a lithium-ion supported media.

Disclosed herein are anolyte materials for redox flow batteries and redox flow batteries comprising the anolyte materials disclosed herein.

The use of the terms "a," "an," "the," and similar referents in the context of describing the invention (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

As used herein, the term "alkyl" refers to straight chained and branched hydrocarbon groups, including but not limited to, methyl, ethyl, n-propyl, i-propyl, n-butyl, sec-butyl, t-butyl, n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 2,3-dimethylbutyl, 3,3-dimethylbutyl, and 2-ethybutyl. The term C$_{m-n}$, means the alkyl group has "m" to "n" carbon atoms. The term "alkylene" refers to an alkyl group having a substituent. An alkyl, e.g., methyl, or alkylene, e.g., —CH$_2$—, group can be substituted with one or more, and typically one to three, of independently selected halo, trifluoromethyl, trifluoromethoxy, hydroxy, alkoxy, nitro, cyano, alkylamino, or amino groups, for example.

As used herein, the term "halo" refers to fluoro, chloro, bromo, and iodo.

The term "hydroxy" is defined as —OH.

The term "alkoxy" is defined as —OR, wherein R is alkyl.

The term "amino" is defined as —NH$_2$, and the term "alkylamino" is defined as —NR$_2$, wherein at least one R is alkyl and the second R is alkyl or hydrogen.

The term "carbamoyl" is defined as —C(=O)NR$_2$.

The term "carboxy" is defined as —C(=O)OH or a salt thereof.

The term "nitro" is defined as —NO$_2$.

The term "cyano" is defined as —CN.

The term "trifluoromethyl" is defined as —CF$_3$.

The term "trifluoromethoxy" is defined as —OCF$_3$.

As used herein, the term "aryl" refers to a monocyclic or polycyclic aromatic group, preferably a monocyclic or bicyclic aromatic group. Examples of aryl groups include, but are not limited to, phenyl, naphthyl, fluorenyl, azulenyl, anthryl, phenanthryl, pyrenyl, biphenyl, and terphenyl. Aryl also refers to bicyclic and tricyclic carbon rings, where one ring is aromatic and the others are saturated, partially unsaturated, or aromatic, for example, dihydronaphthyl, indenyl, indanyl, or tetrahydronaphthyl (tetralinyl). Unless otherwise indicated, an aryl group can be unsubstituted or substituted with one or more, and in particular one to four, groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "benzyl" refers to —CH$_2$-phenyl. Unless otherwise indicated, a benzyl group can be unsubstituted or substituted with one or more, and in particular one to four, groups independently selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "heterocyclic" refers to a heteroaryl and heterocycloalkyl ring systems.

As used herein, the term "heteroaryl" refers to a monocyclic or bicyclic ring system containing one or two aromatic rings and containing at least one nitrogen, oxygen, or sulfur atom in an aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl group has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzothiophenyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quiazolinyl, thiadiazolopyrimidyl, and thienopyridyl. Unless otherwise indicated, a heteroaryl group can be unsubstituted or substituted with one or more, and in particular one to four, substituents selected from, for example, halo, alkyl, alkenyl, —OCF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "cycloalkyl" means a mono-, bi-, or tri-cyclic, saturated or partially unsaturated, ring system containing three to twelve carbon atoms, including cyclopropyl, cyclobutyl, cyclopentyl, cyclohexyl, cycloheptyl, cyclooctyl, and adamantyl optionally substituted with one or more, and typically one to three, of independently selected halo, trifluoromethyl, trifluoromethoxy, hydroxy, alkoxy, nitro, cyano, alkylamino, or amino groups, for example.

As used herein, the term "heterocycloalkyl" means a monocyclic or a bicyclic, saturated or partially unsaturated, ring system containing 4 to 12 total atoms, of which one to five of the atoms are independently selected from nitrogen, oxygen, and sulfur and the remaining atoms are carbon. Nonlimiting examples of heterocycloalkyl groups are azetidinyl, pyrrolidinyl, piperidinyl, piperazinyl, dihydropyrrolyl, morpholinyl, thiomorpholinyl, dihydropyridinyl, oxacycloheptyl, dioxacycloheptyl, thiacycloheptyl, diazacycloheptyl, each optionally substituted with one or more, and typically one to three, of independently selected halo, $C_{1-6}$ alkyl, $C_{1-6}$ alkoxy, cyano, amino, carbamoyl, nitro, carboxy, $C_{2-7}$ alkenyl, $C_{2-7}$ alkynyl, or the like on an atom of the ring.

In one aspect, an anolyte solution for a redox flow battery is provided. The anolyte solution comprises a non-aqueous solvent; a supporting electrolyte; and a compound of formula I as an anolyte material:

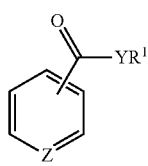
(I)

wherein Y is selected from the group consisting of null, O, and NR$^3$; Z is selected from the group consisting of N, N$^+$O$^-$, N$^+$R$^-$, and

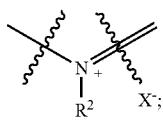

R$^1$ is selected from the group consisting of optionally substituted $C_{1-10}$ alkyl, $C_{3-12}$ cycloalkyl, and optionally substituted phenyl; R$^2$ is selected from the group consisting of optionally substituted $C_{1-10}$ alkyl, $C_{3-12}$ cycloalkyl, and optionally substituted phenyl; R$^3$ is an optionally substituted $C_{1-10}$ alkyl; R is a Lewis acid; and X$^-$ is an anion.

In some embodiments, the compound of formula I has a structure of formula II:

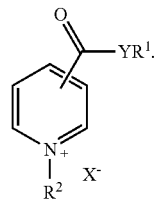
(II)

In various embodiments, the compound of formula I or formula II is substituted with the —C(O)YR$^1$ group at the ortho or para position.

In various embodiments, Y is O.

In various embodiments, R$^3$ is selected from the group consisting of methyl, ethyl, propyl, and butyl.

In various embodiments, the compound of formula I has a structure of formula III:

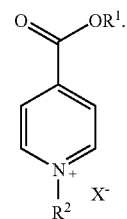
(III)

In various embodiments, R$^2$ is selected from the group consisting of methyl, ethyl, propyl, butyl, and adamantyl.

In various embodiments, R$^2$ is phenyl optionally substituted with one, two, or three $C_{1-5}$ alkyl groups, halo, or $C_{1-5}$ alkyloxy. Suitable R$^2$ groups include, but are not limited to phenyl, 2-methylphenyl, 4-methylphenyl, 2,6-dimethylphenyl, 2,4,6-trimethylphenyl, 4-methoxyphenyl, and 4-chlorophenyl, In various embodiments, R$^1$ is selected from the group consisting of methyl, ethyl, propyl, butyl, adamantyl, and CF$_3$.

In various embodiments, R is selected from the group consisting of boron trihalides, trialkyl boranes, aluminum (III) trihalides, aluminum(III) alkoxides, and phosphorus pentahalides. Suitable R groups include, but are not limited to, BF$_3$, BCl$_3$, AlCl$_3$, AlBr$_3$, and Al(O$^i$Pr)$_3$.

In various embodiments, X$^-$ is selected from the group consisting of I$^-$, Br$^-$, Cl$^-$, F$^-$, PF$_6^-$, BF$_4^-$, $^-$OAc, SO$_4^{2-}$, ClO$_4^-$, NO$_3^-$, alkoxides such as $^-$OMe, CF$_3$SO$_3^-$, CH$_3$C$_6$H$_4$SO$_3^-$, SbF$_6^-$, SCN$^-$, N$_3^-$, CN$^-$, and BPh$_4^-$.

In various embodiments, at least one of R$^1$, R$^2$, and R$^3$ is substituted with a substituent selected from the group consisting of halo, trifluoromethyl, trifluoromethoxy, hydroxy, alkoxy, nitro, cyano, alkylamino, and amino.

Suitable compounds of formula I include, but are not limited to,

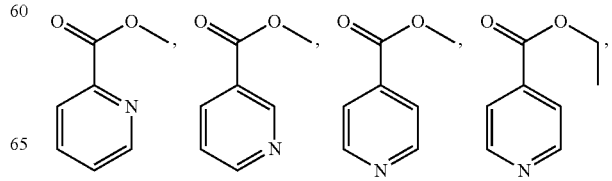

-continued

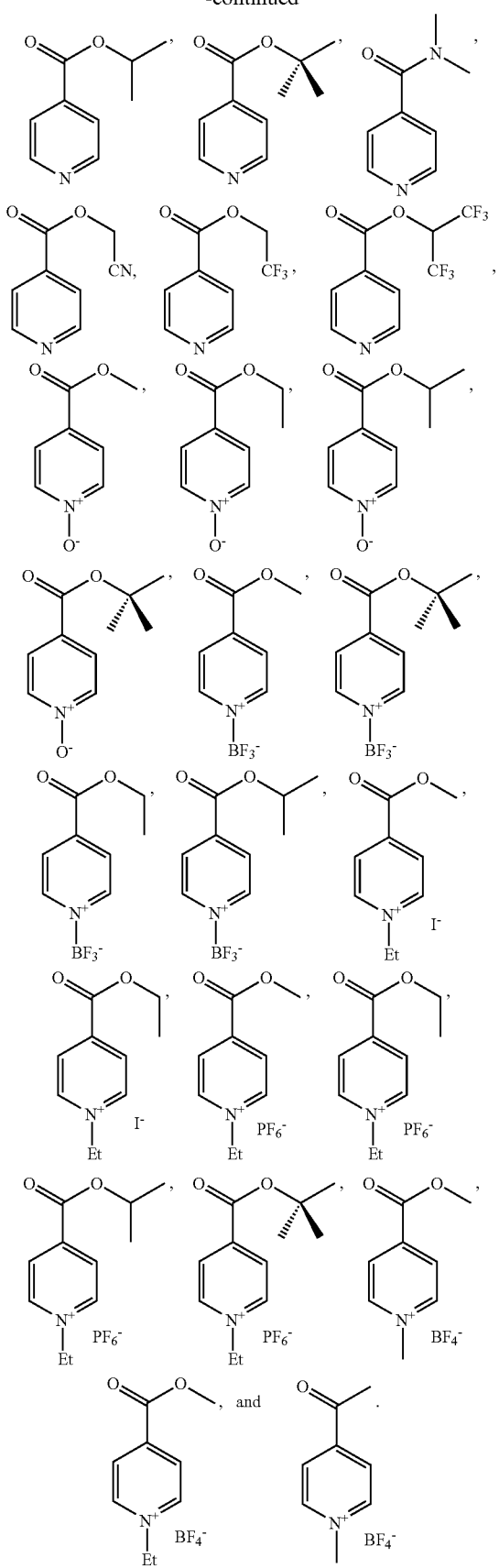

In various embodiments, the compound of formula I has a structure of formula IV:

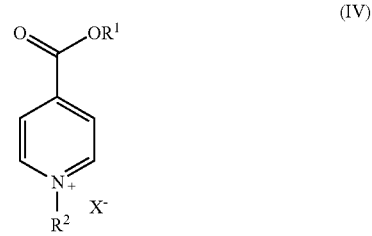

(IV)

wherein $R^1$ is optionally substituted phenyl.

In various embodiments, $X^-$ is selected from the group consisting of $I^-$, $Br^-$, $Cl^-$, $F^-$, $PF_6^-$, $BF_4^-$, $^-OAc$, $SO_4^{2-}$, $ClO_4^-$, $NO_3^-$, alkoxides such as $^-OMe$, $CF_3SO_3^-$, $CH_3C_6H_4SO_3^-$, $SbF_6^-$, $SCN^-$, $N_3^-$, $CN^-$, and $BPh_4^-$.

In various embodiments, $R^1$ is phenyl optionally substituted with one, two, or three $C_{1-5}$ alkyl groups, halo, or $C_{1-5}$ alkyloxy. Suitable $R^1$ groups include, but are not limited to, phenyl, 2-methylphenyl, 4-methylphenyl, 2,6-dimethylphenyl, 2,4,6-trimethylphenyl, 4-methoxyphenyl, and 4-chlorophenyl.

In various embodiments, $R^2$ is selected from the group consisting of methyl, ethyl, propyl, butyl, and adamantyl.

In various embodiments, $R^2$ is optionally substituted phenyl, such as phenyl optionally substituted with one, two, or three $C_{1-5}$ alkyl groups, halo, or $C_{1-5}$ alkyloxy. Suitable $R^2$ groups include, but are not limited to phenyl, 2-methylphenyl, 4-methylphenyl, 2,6-dimethylphenyl, 2,4,6-trimethylphenyl, 4-methoxyphenyl, and 4-chlorophenyl.

Figure 14:
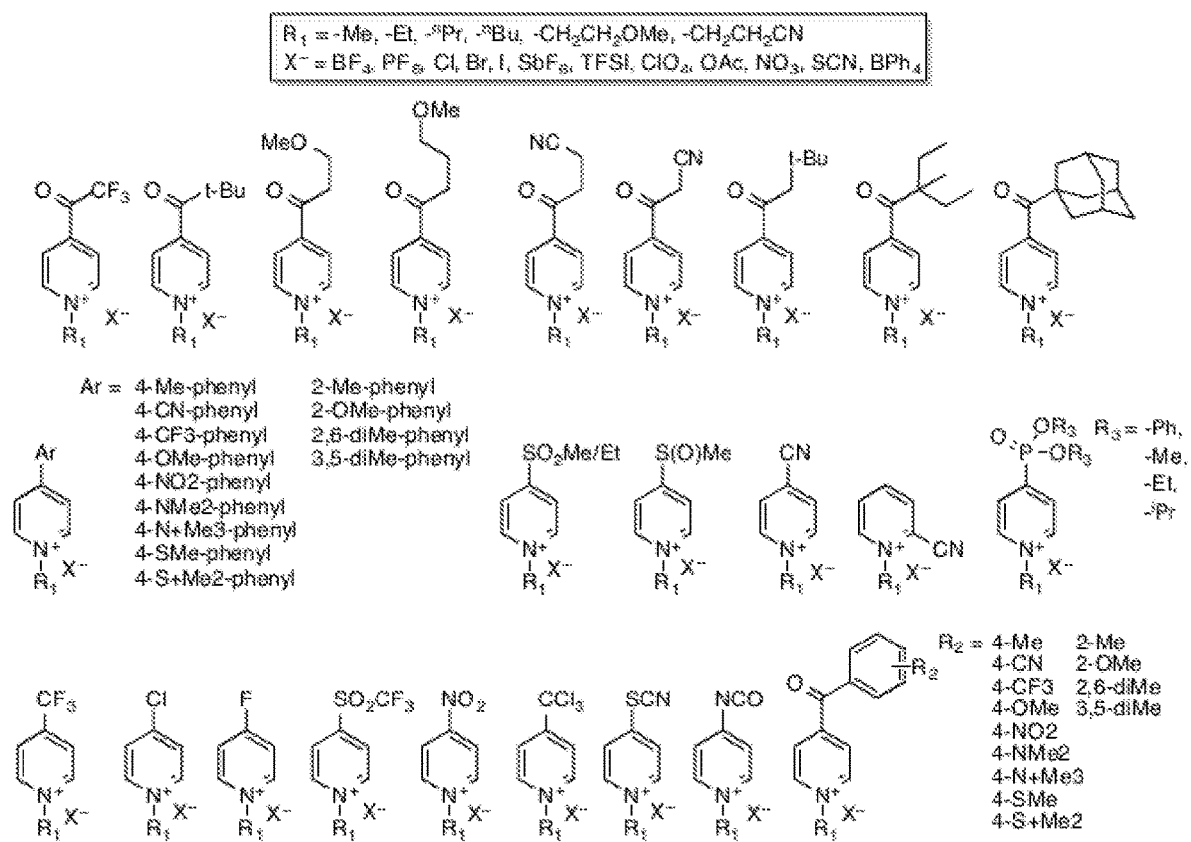
FIG. 14 is a chart showing organic anolyte materials of the invention.
Figure 15:
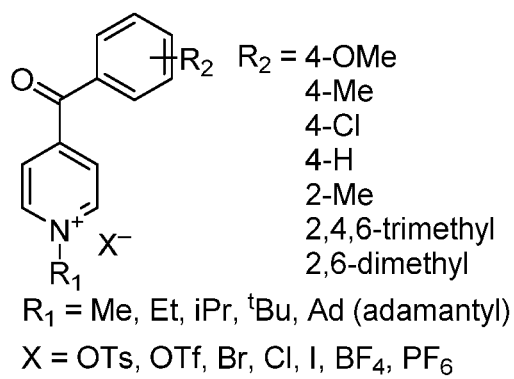
FIG. 15 is a chart showing organic anolyte materials of the invention.
Figure 15:
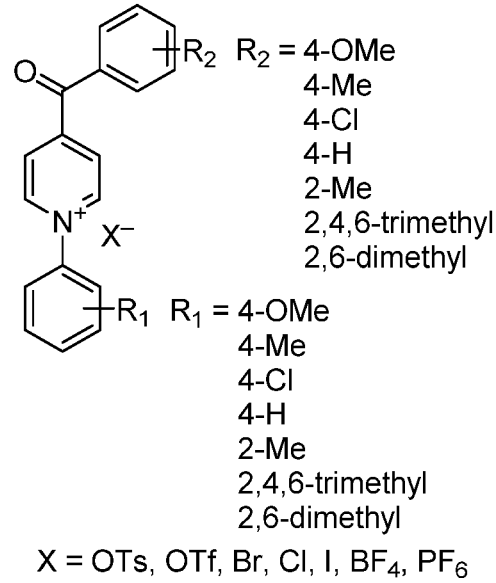
Figure 15:
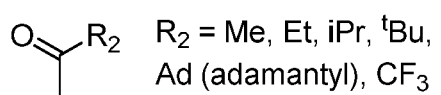
Figure 15:
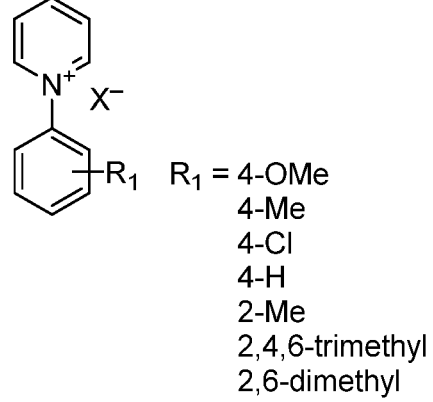
Figure 16:
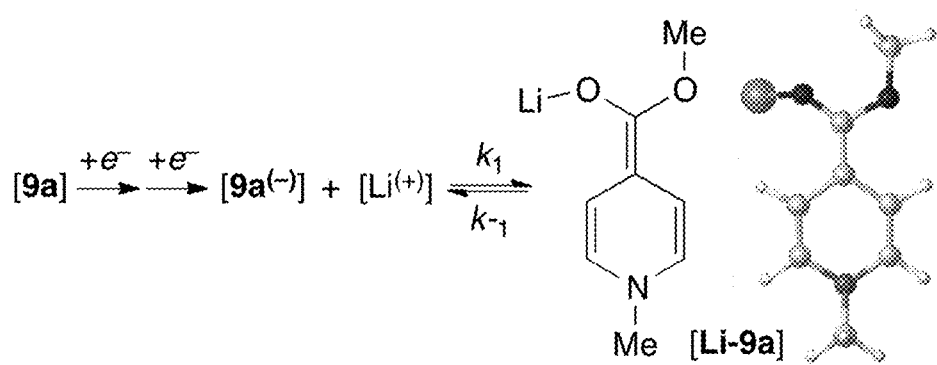
FIG. 16 shows Scheme 1. Coordination of Li+ to Reduced Anolyte 9a(−) and DFT Prediction of Binding Site.

Additional compounds suitable as anolyte materials include, but are not limited to, the compounds provided in FIG. 14 and FIG. 15.

Suitable non-aqueous solvents include, but are not limited to, acetonitrile, acetone, dimethylacetamide, diethyl carbonate, 1,4-dioxane, 1,2-dimethoxy ethane, dichloromethane, 1,2-dichloroethane, nitrobenzene, nitromethane, dimethyl carbonate, dimethyl formamide, 2-methyltetrahydrofuran, tetrahydrofuran, 2,4-dimethyltetrahydrofuran, methoxybenzene, diglyme, γ-butyrolactone, propylene carbonate, ethylene carbonate, N-methyl-2-pyrrolidone, 4-methyl-2-pentanone, acetylacetone, proprionitrile, butryonitrile, isobutyronitrile, benzonitrile, dimethylsulfoxide, sulfolane, dimethylthioformamide, methyl acetate, ethyl acetate, fluoroethylene carbonate, and N,N-dimethylacetamide. Without wishing to be bound by theory, it is believed that non-aqueous solvents facilitate high cell potentials while advantageously avoiding decomposition of the solvent.

Suitable supporting electrolytes include, but are not limited to, electrolytes comprising $Li^+$ such as $LiBF_4$, $LiPF_6$, $LiClO_4$, $LiCF_3SO_3$, and $Li(CF_3SO_2)_2N$, tetrabutylammonium tetrafluoroborate (TBABF$_4$), tetrabutylammonium perchlorate (TBAClO$_4$), tetrabutylammonium hexafluorophosphate (TBAPF$_6$), tetrabutylammonium chloride (TBACl), tetrabutylammonium bromide (TBABr), tetrabutylammonium iodide (TBAI), tetraethylammonium hexafluorophosphate (TEAPF$_6$), tetraethylammonium perchlorate (TEAClO$_4$), tetraethylammonium tetrafluoroborate (TEABF$_4$), NaBF$_4$, NaPF$_6$, trimethylsulfonylchloride, and (NH$_4$)$_2$SO$_4$. Low molecular weight supporting electrolytes such as LiBF$_4$ (MW=94 g/mol) compared to TBABF$_4$ (MW=329 g/mol) advantageously reduce system costs and facilitate improved compatibility.

In some embodiments, the non-aqueous solvent is acetonitrile and the supporting electrolyte is $LiBF_4$.

In another aspect, the disclosure provides a redox flow battery comprising an anolyte solution as disclosed herein. The redox flow battery includes an anode cell comprising an anode and the anolyte solution. The redox flow battery also includes a cathode cell comprising a cathode and a catholyte solution. The redox flow battery can include an ion exchange membrane (e.g., a cation exchange membrane) disposed between the cathode cell and the anode cell. In some embodiments, the redox flow battery includes a catholyte tank connected to the cathode cell and/or an anolyte tank connected to the anode cell.

Synthesis of Compounds Disclosed Herein

The compounds disclosed herein can be prepared following the methods described herein, using suitable modifications to the starting reagents. One of skill in the art, in view of the teachings described herein and using typical organic chemistry techniques, can synthesize a compound as disclosed herein.

In some cases, isonicotinic esters (e.g., 3c, 3d) can be prepared by adding 1,1'-carbonyldiimidazole (CDI) to isonicotinic acid in $CH_2Cl_2$, stirring until evolution of $CO_2$ ceases, and adding an appropriate alcohol.

In some cases, pyridyl N-oxides (e.g., 4a, 4b, 4c, 4d) can be prepared by adding a solution of mCPBA in $CH_2Cl_2$ to an appropriate alkyl isonicotinate in $CH_2Cl_2$.

In some cases, pyridyl $BF_3$-adducts (e.g., 5a, 5b, 5c, 5d) can be prepared by adding $BF_3.Et_2O$ to an appropriate isonicotinate in diethyl ether.

In some cases, N-alkyl alkyl isonicotinate hexafluorophosphate derivatives (e.g., 7a, 7b, 7c, 7d) can be prepared by adding an appropriate iodoalkane to a solution of an appropriate isonicotinate ester in $CH_2Cl_2$, adding $Et_2O$ to precipitate an orange solid, isolating the solid by decanting the liquid, dissolving the solid in water, washing with $Et_2O$, adding $NH_4PF_6$ to a solution of iodide salt (e.g., 6a, 6b) in water, stirring overnight at room temperature, and isolating the white solid that precipitates to obtain the $PF_6$-salt of the alkyl isonicotinate.

In some cases, N-alkyl alkyl isonicotinate tetrafluoroborate derivatives (e.g., 8a, 9a) can be prepared by adding an appropriate alkyl isonicotinate to a solution of triethyloxonium tetrafluoroborate, precipitating a white solid by adding $Et_2O$, isolating by decanting the liquid, redissolving the solid in a minimal amount of $CH_2Cl_2$, precipitating again by adding $Et_2O$, and decanting to yield the desired compound as a white solid.

Redox Flow Batteries

Redox flow batteries are described in U.S. Pat. Nos. 8,927,130, 8,986,862, and 8,642,202, and U.S. Patent Application Publication Nos. 2013/0224538, 2013/266836, and 2014/370403, the entire respective disclosures of which are hereby incorporated by reference.

Compared to conventional batteries, the active material of redox flow batteries is present as ions in an aqueous state rather than a solid state. A redox flow battery typically includes a cathode cell comprising a cathode and a catholyte solution, and an anode cell comprising an anode and an anolyte solution. Generally, the cathode cell is separated from the anode cell by an ion exchange membrane. In some cases, the cathode cell is connected to a cathode tank that supplies a catholyte to the cathode cell. Similarly, in some cases, the anode cell is connected to an anode tank that supplies an anolyte solution to the anode cell. Pumps circulate the catholyte solution and anolyte solution, respectively, from the cathode tank through the cathode cell and from the anode tank through the anode cell. Charging and discharging occur in the cathode and the anode according to a change of oxidation states of ions.

The ion exchange membrane prevents ions of active materials of the catholyte material and the anolyte material from being mixed with each other, while ions of a charge carrier of a supporting electrolyte may be transferred.

A redox flow battery can be discharged by connecting it to an external circuit including an electric load and supplying a current to the external circuit. A redox flow battery can be charged by connecting it to an external power source and supplying a current to the redox flow battery. Generally, a catholyte solution is charged when a redox couple is oxidized to a higher one of two oxidation states, and is discharged when reduced to a lower one of the two oxidation state. Conversely, an anolyte solution is charged when a redox couple is reduced to a lower one of two oxidation states, and is discharged when oxidized to a higher one of the two oxidation states.

In some cases, the anolyte material and/or catholyte material has a weight-to-charge ratio that is less than 200 g/mol/e$^-$, for example, less than 150 g/mol/e$^-$, less than 130 g/mol/e$^-$, less than 120 g/mol/e$^-$, and/or less than 100 g/mol/e$^-$. Suitable catholyte materials include, but are not limited to, molecules with extensive conjugation, such as quinones, thioquinones, arylamines, alkoxyarenes, thiophenes, thiadiazoles, and N-oxides.

FIG. 1 shows half-cell reactions of anolyte and catholyte materials in a lithium-ion supported media. As shown in FIG. 1, lithium electrolytes have differing effects on anolytes versus catholytes. Charged catholyte materials are generally cations and form ion pairs with the anionic-supporting electrolyte (for example, $BF_4^-$ in FIG. 1). In contrast, charged anolytes are generally anions and the cation of the supporting electrolyte balances the half-cell charge. As a result, the choice of supporting electrolyte [i.e., $Li^+$ vs. $NBu_4^+$ salt] has a minimal impact on the electrochemistry of the catholyte material but a significant effect on the electrochemistry of the anolyte material.

The following examples are not intended to be limiting but only exemplary of specific embodiments of the invention.

EXAMPLES

Example 1 Electrochemical Evaluation of Compounds

The electrochemistry of a series of heteroarenes was evaluated by cyclic voltammetry (CV). Electrochemical analysis was performed in the absence of oxygen and moisture. The experiments were conducted in a three-electrode cell comprised of a glassy carbon working electrode, a platinum counter electrode, and a $Ag/Ag^+$ reference electrode. The CV of each anolyte candidate was initially conducted in acetonitrile (MeCN) with tetrabutylammonium tetrafluoroborate ($TBABF_4$) as the supporting electrolyte. These results were then compared to those obtained with $LiBF_4$ as the supporting electrolyte under otherwise identical conditions.

Figure 2:
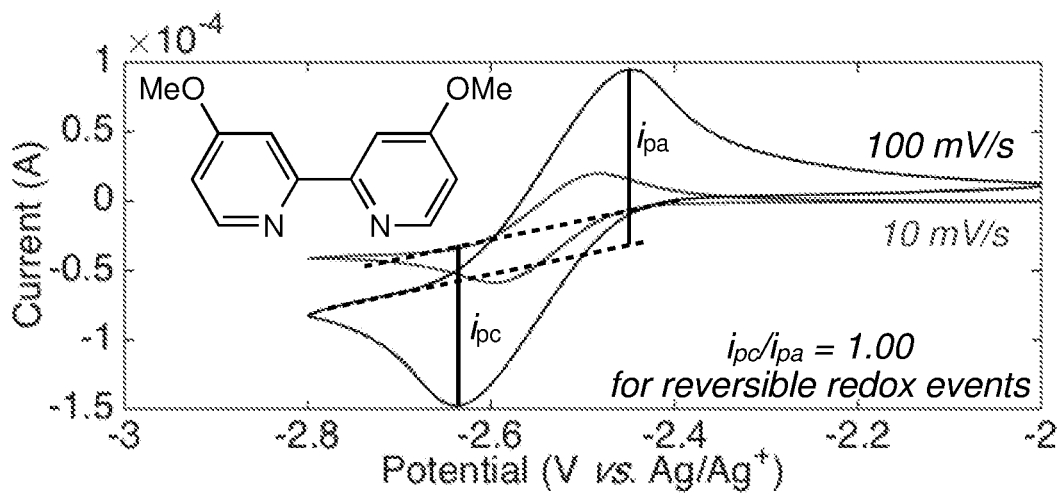
FIG. 2 is a graph showing the reductive couple of 4,4'-methoxybipyridine (0.01 M) in MeCN with $TBABF_4$ (0.1 M) at 100 and 10 mV/s scan rates (2nd cycles plotted).

The reversibility of each redox couple in the CV was estimated by calculating the ratio of the diffusion-limited peak-heights of the cathodic (ipc) and anodic (ipa) currents (FIG. 2). The current peak heights were determined from the second CV cycle, and are all reported following deconvolution of the current-potential plot. Reversible redox processes that generate reduced species with high persistence and stability generally exhibit current peak-heights ratios equal to one (ipc/ipa=1). In addition, potentiometry conducted at slow scan rates allows for an extended lifetime of the reduced species (FIG. 2, 10 mV/s scan). With longer lifetimes, the concentration of charged anolytes that are susceptible to irreversible chemical or electrochemical reactions will decrease, and lower current responses upon re-oxidation will be observed. As a result, redox couples measured at slow scan rates generally occur with current peak-height ratios that deviate from unity to a greater extent than couples measured at faster scan rates. Thus, these techniques provide a method to rapidly assess and compare a range of anolyte materials.

A number of unligated-pyridines were found to exhibit reversible electrochemistry. Specifically, the reduction of 4,4'-methoxy bipyridine occurs reversibly at low potential (−2.6 V versus Ag/Ag+ in MeCN with NBu$_4$BF$_4$ supporting electrolyte; FIG. 2).

Example 2 Evaluation of Pyridine Derivatives as Anolytes

The CV of various low molecular weight analogues of 4,4'-methoxybipyridine (216 MW/e) in MeCN with NBu$_4$BF$_4$ as the supporting electrolyte was assessed. Pyridine derivatives bearing an electron-donating group (EDG) at the 2- or 4-position (4-methoxypyridine, 2-methoxypyridine, 4-methylpyridine, 2-methylpyridine) were assessed and no reduction was observed within the electrochemical window of MeCN.

Next, pyridine derivatives bearing lower molecular weight electron withdrawing substituents conjugated with the pyridine ring were assessed. The redox potentials and current peak-height ratios at scan rates of 100 and 10 mV/s were determined for a series of picolinate (1), nicotinate (2), and isonicotinate (3a-h) derivatives (Table 1). These pyridyl esters are attractive targets because most are liquids that are miscible with MeCN. In addition to the possibility for achieving high concentrations of anolyte, many of these pyridines are already produced on large scale.

TABLE 1

Ratios of Current Peak Heights from CV for Isonicotinates

| Compound[a] | Structure | Solvent/support[b] | $E_1^0(V)^c$ | $i_{pc1}/i_{pa1}^d$ (100 mV/s) | $i_{pc1}/i_{pa1}^d$ (10 mV/s) |
|---|---|---|---|---|---|
| 1a | (structure) | MeCN/TBABF$_4$ | −2.36 | 1.83 | >5 |
| 2a | (structure) | MeCN/TBABF$_4$ | —[e] | >5 | >5 |
| 3a | (structure) | MeCN/TBABF$_4$ | −2.16 | 1.15 | 1.67 |
| 3b | (structure) | MeCN/TBABF$_4$ | −2.20 | 1.03 | 1.28 |
| 3c | (structure) | MeCN/TBABF$_4$ | −2.20 | 1.02 | 1.10 |

TABLE 1-continued

Ratios of Current Peak Heights from CV for Isonicotinates

| Compound[a] | Structure | Solvent/support[b] | $E_1^0(V)$[c] | $i_{pc1}/i_{pa1}$[d] (100 mV/s) | $i_{pc1}/i_{pa1}$[d] (10 mV/s) |
|---|---|---|---|---|---|
| 3d | tert-butyl isonicotinate | MeCN/TBABF$_4$ | −2.24 | 1.01 | 1.09 |
| 3e | N,N-dimethyl isonicotinamide | MeCN/TBABF$_4$ | −2.52 | 1.18 | >5 |
| 3f | cyanomethyl isonicotinate | MeCN/TBABF$_4$ | —[e] | >5 | >5 |
| 3g | 2,2,2-trifluoroethyl isonicotinate | MeCN/TBABF$_4$ | −2.03 | 1.91 | >5 |
| 3h | 1,1,1,3,3,3-hexafluoroisopropyl isonicotinate | MeCN/TBABF$_4$ | —[e] | >5 | >5 |
| 3a | methyl isonicotinate | PC/TBABF$_4$ | −2.62 | 1.35 | 2.02 |
| 3a | methyl isonicotinate | MeCN/LiBF$_4$ | —[e] | >5 | >5 |

TABLE 1-continued

Ratios of Current Peak Heights from CV for Isonicotinates

| Compound[a] | Structure | Solvent/support[b] | $E_1^0(V)$[c] | $i_{pc1}/i_{pa1}$[d] (100 mV/s) | $i_{pc1}/i_{pa1}$[d] (10 mV/s) |
|---|---|---|---|---|---|
| 3a | 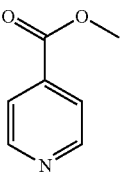 | PC/LiBF$_4$ | —[e] | >5 | >5 |

[a] 0.01M substrate.
[b] 0.10M TBABF$_4$ or LiBF$_4$ support.
[c] $E_1^0$ is calculated as $(E_{1c} + E_{1a})/2$.
[d] Ratios were calculated for the 2nd cycle following deconvolution of the voltammogram.
[e] No anodic current was observed.

The position of the ester moiety was varied in methyl carboxylate analogues 1a, 2a and 3a. In MeCN/TBABF$_4$, all three compounds underwent reduction at equilibrium potentials lower than −2 V (Table 1). No re-oxidation current was observed for methyl picolinate 1a. Methyl nicotinate 2a showed a quasi-reversible couple at 100 mV/s, but this couple was completely irreversible at the slower 10 mV/s scan rate. In contrast, methyl isonicotinate 3a exhibited a reversible redox couple even at 10 mV/s scan rate (Table 1). Without wishing to be bound by theory, this propensity for reversible redox couples of pyridines bearing alkyl carboxylate substituents at the 2- and 4-positions, rather than 3-position, is believed to be consistent with delocalization of the added electron through orbital conjugation of the carbonyl π-orbital and nitrogen p-orbital.

The impact of the ester substituent on the electrochemical behavior of isonicotinates 3a-h was assessed. The methyl, ethyl, isopropyl, and tert-butyl esters all showed reversible reductions at comparable potentials (approximately −2.2 V). A sequential improvement in current peak-height ratio was observed upon moving from the methyl (3a) to ethyl (3b) to isopropyl (3c) to tert-butyl (3d) derivative (Table 1 and FIG. 3). In contrast, esters bearing the electron withdrawing cyanoethyl (3f), trifluoroethyl (3g), and hexafluoroisopropyl (3h) substituents showed highly irreversible reductions (at approximately −2.0 V), even at fast scan rates. Replacement of the ester with a dimethylamide substituent (3e) resulted in a significant lowering of the reduction potential (−2.52 V); however, this redox couple was quasi-reversible at scan rates of 100 mV/s and irreversible at slower scan rates.

Figure 4:
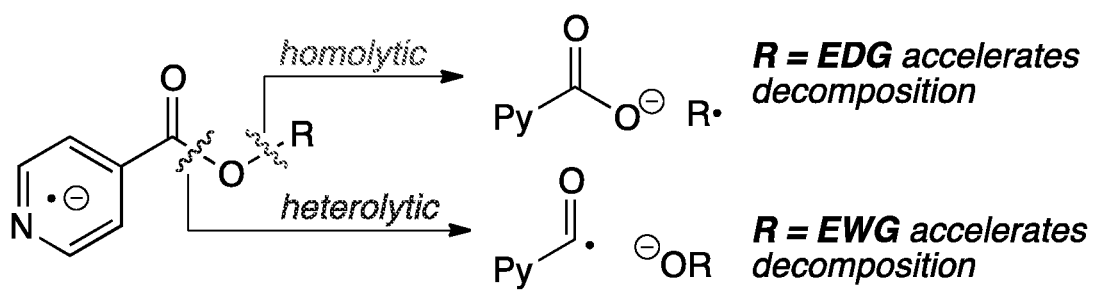
FIG. 4 is a schematic drawing showing two possible decomposition pathways for the reduced anolytes (isonicotinate radical anions).

As shown in Table 1, isonicotinates bearing electron-withdrawing groups (EWGs) (3f-h) exhibit irreversible electrochemistry. Furthermore, the reduction of the tert-butyl analogue 3d shows enhanced reversibility relative to that of the methyl analogue 3a. Without wishing to be bound by theory, these data are believed to be more consistent with the heterolytic decomposition pathway shown in FIG. 4.

Figure 3:
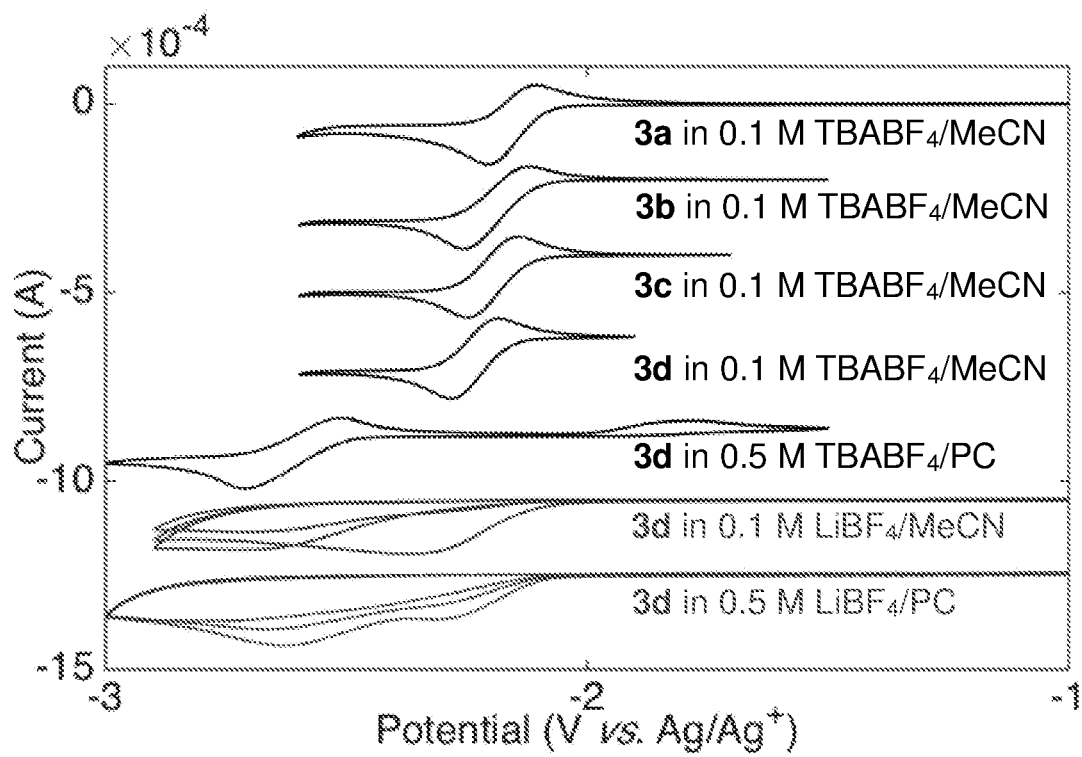
FIG. 3 is a graph showing voltammograms of compounds 3a, 3b, 3c, 3d (0.01 M) in the specified media at 10 mV/s scan rate (2nd cycles plotted).

Example 3 Evaluation of N-Oxides and BF$_3$-Adducts of Isonicotinates as Anolytes CV of compound 3d with LiBF$_4$ as the supporting electrolyte was performed. No reversible reduction processes were observed at scan rates between 10 and 500 mV/s in acetonitrile or propylene carbonate (PC) (FIG. 3). The cathodic wave in FIG. 3 suggests that reduction does occur under these conditions to generate a similar radical anion as that in TBABF$_4$. Without wishing to be bound by theory, it is believed that the irreversible electrochemistry is likely due to interactions between this radical anion and the Li$^+$ in the support and that one possible site for Li$^+$ interaction is at the Lewis basic nitrogen atom of the isonicotinate. To assess whether the reversibility of this reduction in the presence of LiBF$_4$ is effected by masking this site via N-functionalization, alkyl isonicotinate-N-oxides 4a-d were examined. These compounds are particularly attractive due to the low molecular weight of the oxygen atom that serves as the protecting group. As shown in Table 2, these compounds demonstrated reversible reduction in MeCN with TBABF$_4$ supports. However, their reduction is irreversible with LiBF$_4$ as the supporting electrolyte (Table 2). Without wishing to be bound by theory, it is believed that coordination of Li$^+$ to the oxygen of the N-oxide is possible in this system.

TABLE 2

Ratios of Current Peak Heights from CV for N-Oxides and BF$_3$-Adducts of Isonicotinates

| Compound[a] | Structure | Solvent/support[b] | $E_1^0(V)$[c] | $i_{pc1}/i_{pa1}$[d] (100 mV/s) | $i_{pc1}/i_{pa1}$[d] (10 mV/s) |
|---|---|---|---|---|---|
| 4a | 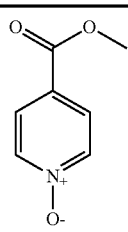 | MeCN/TBABF$_4$ | −1.96 | 1.05 | 1.41 |

TABLE 2-continued

Ratios of Current Peak Heights from CV for N-Oxides and BF$_3$-Adducts of Isonicotinates

| Compound[a] | Structure | Solvent/support[b] | $E_1^0$(V)[c] | $i_{pc1}/i_{pa1}$[d] (100 mV/s) | $i_{pc1}/i_{pa1}$[d] (10 mV/s) |
|---|---|---|---|---|---|
| 4d | tert-butyl isonicotinate N-oxide | MeCN/TBABF$_4$ | −2.01 | 1.00 | 1.17 |
| 4a | methyl isonicotinate N-oxide | MeCN/LiBF$_4$ | —[e] | >5 | >5 |
| 4b | ethyl isonicotinate N-oxide | MeCN/LiBF$_4$ | —[e] | >5 | >5 |
| 4c | isopropyl isonicotinate N-oxide | MeCN/LiBF$_4$ | —[e] | >5 | >5 |
| 4d | tert-butyl isonicotinate N-oxide | MeCN/LiBF$_4$ | —[e] | >5 | >5 |
| 5a | methyl isonicotinate BF$_3$-adduct | MeCN/TBABF$_4$ | −1.42 | 1.03 | 1.10 |

TABLE 2-continued

Ratios of Current Peak Heights from CV for N-Oxides and BF$_3$-Adducts of Isonicotinates

| Compound[a] | Structure | Solvent/support[b] | $E_1^0(V)$[c] | $i_{pc1}/i_{pa1}$[d] (100 mV/s) | $i_{pc1}/i_{pa1}$[d] (10 mV/s) |
|---|---|---|---|---|---|
| 5d | [structure: isonicotinate tert-butyl ester, N-BF$_3$] | MeCN/TBABF$_4$ | −1.45 | 1.03 | 1.05 |
| 5a | [structure: isonicotinate methyl ester, N-BF$_3$] | MeCN/LiBF$_4$ | −1.83 | 1.02 | 1.06 |
| 5b | [structure: isonicotinate ethyl ester, N-BF$_3$] | MeCN/LiBF$_4$ | −1.80 | 1.06 | 1.08 |
| 5c | [structure: isonicotinate isopropyl ester, N-BF$_3$] | MeCN/LiBF$_4$ | −1.80 | 1.06 | 1.09 |
| 5d | [structure: isonicotinate tert-butyl ester, N-BF$_3$] | MeCN/LiBF$_4$ | −1.84 | 1.06 | 1.11 |

[a] 0.01M substrate.
[b] 0.10M TBABF$_4$ or LiBF$_4$ support.
[c] $E_1^0$ is calculated as $(E_{1c} + E_{1a})/2$.
[d] Ratios were calculated for the 2nd cycle following deconvolution of the voltammogram.
[e] No anodic current was observed.

Isonicotinate adducts in which the nitrogen is protected with functional groups that cannot bind to Li$^+$ (5a-5d) were also assessed. Lewis acidic BF$_3$ was employed as a protecting group for the pyridine nitrogen. Without wishing to be bound by theory, it is believed that after coordination of the BF$_3$ to N, this protecting group is unreactive towards Li-complexation. A series of isonicotinate-BF$_3$-adducts were synthesized (5a-5d), and the results from CV analyses of these molecules are summarized in Table 2. Low potential couples of the methyl and tert-butyl analogues 5a and 5d, respectively, were initially examined in TBABF$_4$ supports. Current peak-height ratios approaching unity were observed for both materials. In addition, similar current ratios were observed for CVs performed with Li-ion supporting electrolytes (Table 2). Furthermore, the current ratios remained close to unity even when measured at the slow 10 mV/s scan rate.

Figure 5:
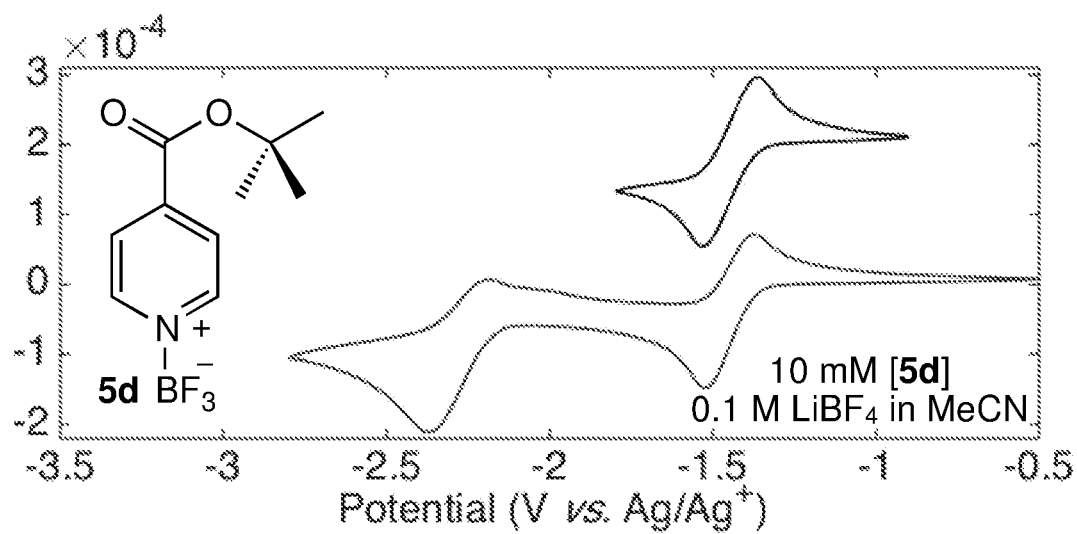
FIG. 5 is a graph showing cyclic voltammograms of 5d through one (upper trace) and two (lower trace) redox couples with $LiBF_4$ as a supporting electrolyte at 100 mV/s scan rate.

The molecular weight to charge ratio of BF$_3$ adduct 5d is 247 g/mol/e−. To assess whether a molecular weight to charge ratio of 150 g/mol/e− or less could be obtained, more negative potentials were scanned to explore the possibility of charging 5d with an additional electron. Minimal re-oxidation was observed after the second reduction, as illustrated by the lower trace in FIG. 5. These data demonstrate that organic compounds can undergo reversible processes at low potentials in the presence of Li-ion supporting electrolytes if they are appropriately functionalized to mitigate $Li^+$ interaction with reduced anolyte.

Example 4 Evaluation of N-Alkyl Pyridinium Salts as Anolytes

Other blocking substituents on nitrogen were assessed. In particular, N-alkyl pyridinium salts, which have a stronger N-alkyl bond compared to a $BF_3$-adduct, were assessed. Advantageously, N-alkyl pyridinium salts are readily accessible through single step syntheses and are stable on the benchtop. The isonicotinates were subjected to iodoethane to form the N-ethyl pyridinium iodide salts 6a-b. CV of these pyridinium salts in MeCN with 0.1 M $LiBF_4$ revealed a reversible redox couple at −1.10 V with peak height ratios of nearly one, as shown in Table 3. Scanning to more negative potentials with 6a revealed a second couple occurring at −1.85 V. Unlike the $BF_3$-adducts, these N-alkyl salts exhibited a large anodic peak after this second reduction Like the first couple, the peak-heights of currents at the second couple are nearly equal with a ratio of 0.95 at scan rates of 10 mV/s.

TABLE 3

Ratios of Current Peak Heights for Isonicotinates as Determined by Cyclic Voltammetry

| Compound[a] | Structure | Solvent/support[b] | $E_1^0(V)^c$ | $i_{pc1}/i_{pa1}^e$ (10 mV/s) | $E_2^0(V)^d$ | $i_{pc2}/i_{pa2}^e$ (10 mV/s) |
|---|---|---|---|---|---|---|
| 6a | methyl isonicotinate N-Et, I⁻ | MeCN/LiBF₄ | −1.11 | 0.99 | −1.85 | 0.95 |
| 6b | ethyl isonicotinate N-Et, I⁻ | MeCN/LiBF₄ | −1.10 | 0.98 | −1.86 | 0.94 |
| 7a | methyl isonicotinate N-Et, PF₆⁻ | MeCN/LiBF₄ | −1.11 | 0.98 | −1.88 | 0.96 |
| 7b | ethyl isonicotinate N-Et, PF₆⁻ | MeCN/LiBF₄ | −1.11 | 0.99 | −1.90 | 0.96 |
| 7c | isopropyl isonicotinate N-Et, PF₆⁻ | MeCN/LiBF₄ | −1.13 | 0.97 | −1.89 | 0.95 |

TABLE 3-continued

Ratios of Current Peak Heights for Isonicotinates as Determined by Cyclic Voltammetry

| Compound[a] | Structure | Solvent/support[b] | $E_1^0(V)$[c] | $i_{pc1}/i_{pa1}$[e] (10 mV/s) | $E_2^0(V)$[d] | $i_{pc2}/i_{pa2}$[e] (10 mV/s) |
|---|---|---|---|---|---|---|
| 7d | 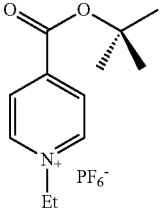 | MeCN/LiBF$_4$ | −1.15 | 0.99 | −1.93 | 0.93 |
| 8a | 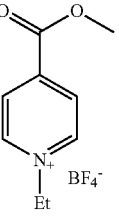 | MeCN/LiBF$_4$ | −1.11 | 0.98 | −1.89 | 0.95 |
| 7a[f] | 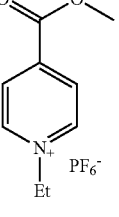 | MeCN/LiBF$_4$ | −1.12 | 1.02[f] | −1.91 | 1.08[f] |
| 7d[f] | 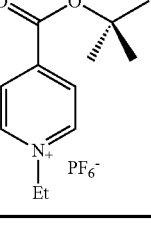 | MeCN/LiBF$_4$ | −1.14 | 1.09[f] | −1.92 | 1.38[f] |

[a] 0.01M substrate.
[b] 0.10M LiBF$_4$ support.
[c] $E_1^0$ is calculated as $(E_{1c} + E_{1a})/2$.
[d] $E_2^0$ is calculated as $(E_{2c} + E_{2a})/2$.
[e] Ratios were calculated for the 2nd cycle following deconvolution of the voltammogram.
[f] CV measured at 200 mV/s scan rate.

Voltammograms of the iodide salts displayed an additional current response at lower potentials. Without wishing to be bound by theory, it is believed that this response might result from redox processes of the iodide counterion.

Hexafluorophosphate (PF$_6$) analogues 7a-d were prepared by salt metathesis of the iodide salts with NH$_4$PF$_6$. Voltammograms of these compounds were much cleaner than those of the iodide analogues, and the redox potentials and current peak height ratios were nearly identical (Table 3).

BF$_4$ analogue 8a was prepared and the compound demonstrated identical electrochemical properties to those of 6a and 7a, but a significantly lower MW (122 g/mol/e−) (Table 3).

Substitution of the carboxylate of the N-ethyl isonicotinates 7a-d did not influence the current peak height ratios for the two redox couples. Compounds 7a-d all show ratios of close to one at 10 mV/s (Table 3). However, surprisingly, CVs measured at a faster 200 mV/s scan rate for compounds 7a and 7d reveal current ratios that were farther from unity than those measured at 10 mV/s (Table 3). Without wishing to be bound by theory, it is believed that additional chemical processes occur during the electrochemical reduction of N-alkyl isonicotinates in LiBF$_4$ supports.

Example 5 Electrolyte Effects on the Potentiometry of N-Alkyl Isonicotinates

Figure 6:
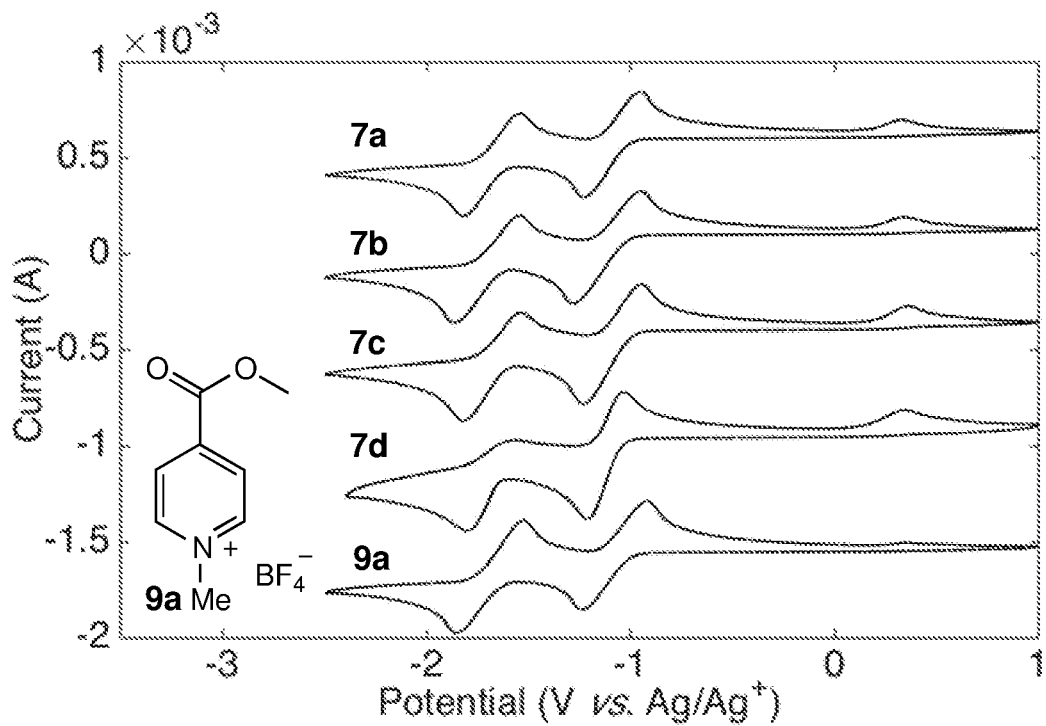
FIG. 6 is a graph showing cyclic voltammograms of 7a, 7b, 7c, 7d, and 9a (0.01 M) in MeCN with 0.1 M LiBF$_4$ at 200 mV/s scan rate (2nd cycles are plotted).

A potentiometric study of a solution of 7a over a wider range of potentials (+1 V to −2.5 V) was conducted. The voltammograms revealed an anodic peak at +0.4 V with no corresponding cathodic current (FIG. 6, trace for 7a). Compounds 7b-d were subjected to identical conditions, and the resulting CVs show an increase in the magnitude of the anodic couple at +0.4 V as the number of carbon atoms of the carboxylate alkyl groups increased (i.e. Me<Et<iPr<tBu). In addition, the increase in magnitude of the anodic couple at +0.4 V appears to coincide with a decrease in the magnitude of the anodic couple at −1.8 V. Without wishing to be bound by theory, it is believed that the new peak at positive potential is the result of a chemical or electrochemical reaction of the doubly-reduced N-alkyl isonicotinate.

Figure 7:
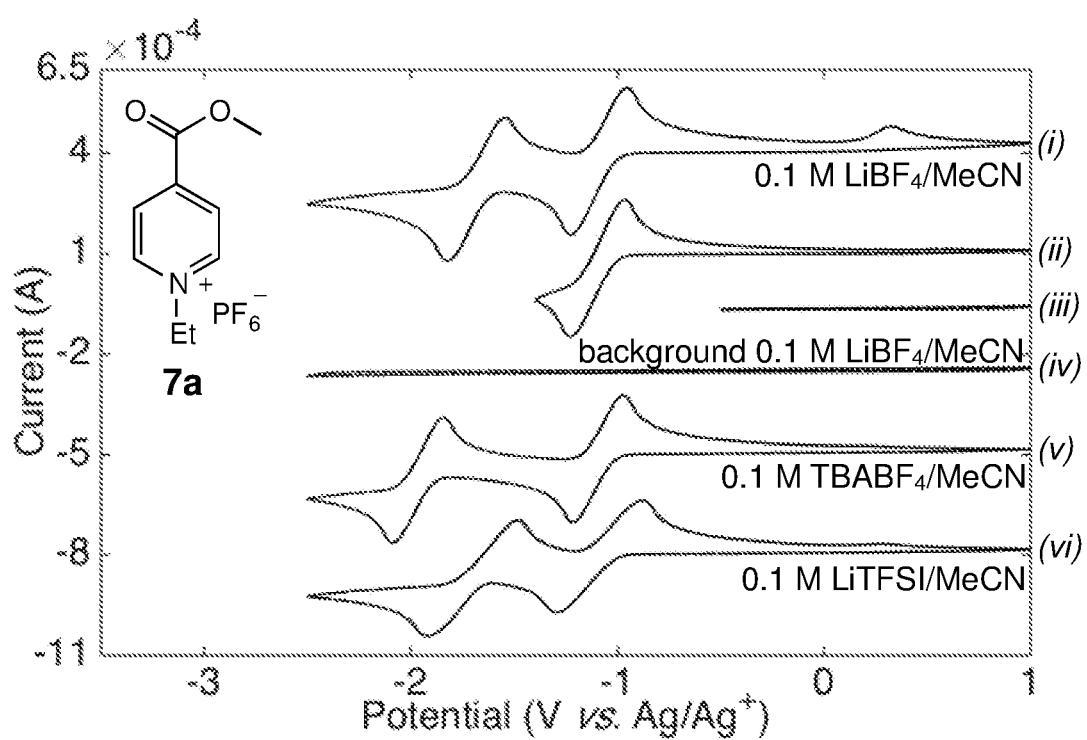
FIG. 7 is a graph showing cyclic voltammograms of 7a (0.01 M) in MeCN using different sweep width (i-iii) and supporting electrolyte (v-vi) at 200 mV/s scan rate (2nd cycles are plotted).

The identity of the species that leads to the anodic peak at positive potentials was probed through the series of experiments summarized in FIG. 7. Voltammogram (i) was generated by potentiometric scanning of a solution of compound 7a in MeCN with LiBF$_4$ electrolyte from an initial potential of +1 V to a low potential of −2.5 V and back to +1 V. Analogous CVs were then acquired with an identical solution using −1.4 V (ii) or −0.5 V (iii) as the lower limits of the scanning potentials. In these latter two experiments, no current peaks were observed at positive potentials. In addition, a CV of LiBF$_4$ in MeCN without anolyte over the full potential window revealed only baseline signals (iv). Without wishing to be bound by theory, it is believed that the anodic current at +0.4 V results from a species that forms following the second reductive couple at −1.9 V. It was also observed that the magnitude of this anodic current is dependent on the concentration of the supporting LiBF$_4$ electrolyte, with larger magnitudes observed at higher concentrations. The choice of electrolyte salt also influenced the observed current response at high potentials. For example, no high potential peak is observed in the CV of 7a with TBABF$_4$ as the electrolyte (v), while only a small high potential peak is observed with lithium bis-trifluoromethane sulfonamide (LiTFSI) as the support (vi).

Without wishing to be bound by theory, it is believed that the material responsible for the anodic current at +0.4 V is not formed by a simple first-order decomposition of the doubly-reduced anolyte, that the electrochemistry of the reduced anolyte is reversible by CV, and that the unknown species at +0.4 V is formed specifically in the presence of Li$^+$. Further, without wishing to be bound by theory, it is believed that after two reductions, the N-alkyl pyridinium 7a exists as an anion (7a$^{(-)}$), that the anion could form an ion-pair with Li$^+$ in solution, and that it is this ion pair (or Li-adduct) that is oxidized at high potentials. Consistent with this proposal, no anodic current at high potential is observed during electrolysis in the presence of the weakly-coordinating cation TBA$^+$ because a discrete ion-pair does not form (FIG. 7, v). Furthermore, the formation of an ion-pair between the charged anolyte and Li$^+$ is impaired when the counterion of the lithium-ion electrolyte is more coordinating than BF4$^-$ (e.g., TFSF, FIG. 7, vi).

Example 6 Studies and Simulations of Li$^+$-Binding to Charged Anolytes

Depletion of the charged anolyte through formation of adducts could severely limit the cycle lifetime or energy efficiency of an EES. Specifically, batteries with anolytes that irreversibly react with lithium ions will exhibit rapid capacity fade. In addition, the cell potential and energy efficiency of an ESS will be greatly diminished if the charging of anolyte 7a occurs at −1.7 V, but the discharge occurs as the oxidation of the lithium adduct at +0.4 V. To address these issues, other derivatives of N-alkyl isonicotinates we explored in order to limit the formation of the lithium-adducts under conditions with LiBF$_4$ as electrolyte. The experiments in FIG. 6 show that the magnitude of the +0.4 V peak in the CV increases for alkylisonicotinates bearing more highly alkyl-substituted esters (Me<Et<iPr<tBu). An increase in the magnitude of current indicates that formation of the lithium-adduct is more favorable for compounds with more substituted esters. Without wishing to be bound by theory, it is believed that the increased electron-donor ability of tert-butyl groups versus methyl groups enhances Li$^+$ coordination to the doubly reduced species.

Next, molecule 9a was assessed. CV analysis of 9a indicated minimal lithium adduct formation, as almost no current was detected at +0.4 V (FIG. 6, bottom). These results demonstrate that the majority of the charged anolyte 9a($^-$) is oxidized (i.e., discharged) at a low −1.7 V potential.

Density functional theory (DFT) calculations were conducted to probe possible coordination modes of Li$^+$ in the Li-9a adduct. Ground state geometry optimization of this intermediate was conducted with the B3LYP functional using a 6–31+G(d) basis set for all atoms. An implicit solvation model of MeCN was employed, and free energies were determined at 298 K. The DFT calculation predicted that the most stable isomer of Li-9a involves Li$^{30}$ coordination to the carbonyl oxygen in a K$^1$-binding mode, as illustrated in Scheme 1. Without wishing to be bound by theory, the observed influence of the ester substituent on the extent of Li-adduct formation is believed to be consistent with an interaction of Li$^+$ at the carbonyl oxygen.

Figure 8:
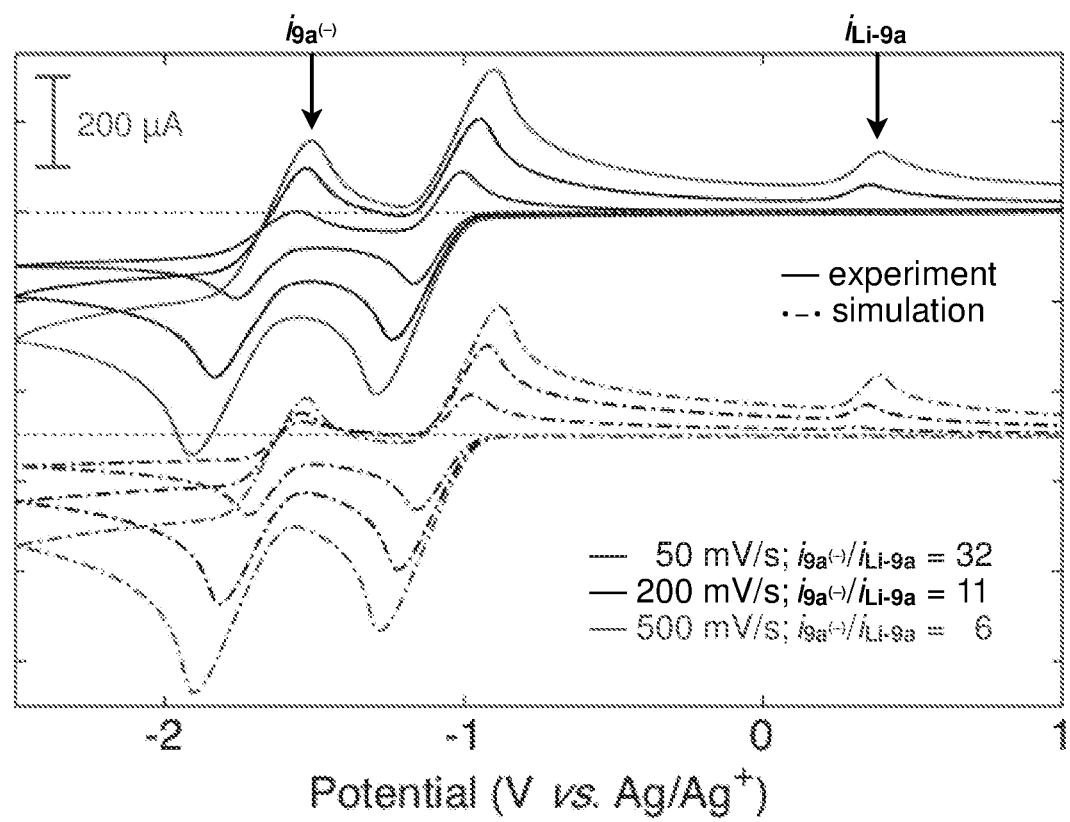
FIG. 8 is a graph showing cyclic voltammograms of 9a (0.01 M) in MeCN with 0.1 M LiBF$_4$ (2nd cycles are plotted).

The reversibility of the binding process illustrated in Scheme 1 was investigated. In an energy storage system, a reversible binding process would be preferred to irreversible formation of Li-9a (k$_1$>>k$_{-1}$). To test the reversibility of Li$^+$ binding, CV on solutions of 9a with 0.1 M LiBF$_4$ in MeCN at scan rates ranging from 50 to 500 mV/s were conducted (FIG. 8, solid lines). The current peak-height that corresponds to the oxidation of 9a$^{(-)}$ (i$_{9a(-)}$) to the current peak-height from oxidation of Li-9a (i$_{Li-9a}$) was compared. At scan rates of 500 mV/s, the ratio of the anodic current associated with 9a$^{(-)}$ to that associated with Li-9a was 6. The current ratios of i$_9$a(−)/i$_{Li-9}$a increased with slower scan rates of 200 and 50 mV/s to 11 and 32, respectively.

Without wishing to be bound be theory, it is believed that at slow scan rates, Li-9a would be in rapid equilibrium with the free anolyte 9a$^{(-)}$, and that as 9a$^{(-)}$ is consumed during the anodic sweep at −1.7 V, Li-9a dissociates to generate additional 9a$^{(-)}$, which is then oxidized. Further, without wishing to be bound be theory, it is believed that at higher scan rates, the potential rapidly reaches+0.4 V, and Li-9a is oxidized before all of 9a$^{(-)}$ can be oxidized at the −1.7 V couple. Thus, Li-9a can be considered as a reservoir for 9a$^{(-)}$, and the anodic peak associated with oxidation of Li-9a is undetectable at scan rates less than 50 mV/s.

Figure 9A:
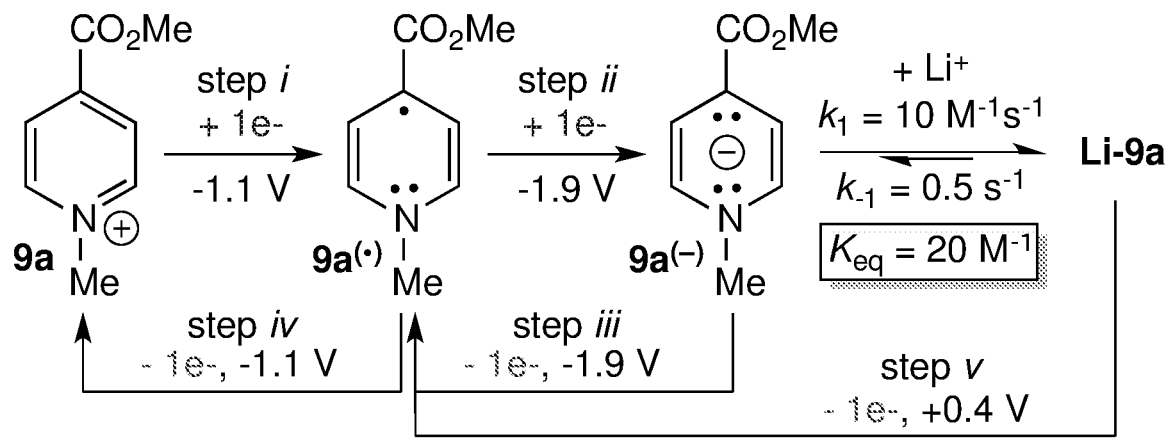
FIG. 9a is a scheme showing potential intermediates generated from −2.5 V to +1 V.

A summary of the proposed speciation of the anolyte at variable potentials is shown in FIG. 9a. A cathodic sweep, starting at +1 V, effects single-electron reductions at −1.1 V and −1.9 V (steps i and ii, respectively) to generate the charged anolyte 9a$^{(-)}$. The potential reaches a minimum at −2.5 V and reverses to increasing potentials. During this time, 9a$^{(-)}$ binds Li$^+$ with an unknown rate constant to generate an unknown concentration of Li-9a. Once the potential increases to −1.9 V, 9a$^{(-)}$ is oxidized to 9a$^{(•)}$ (step iii), and 9a is regenerated by subsequent oxidation at −1.1 V (step iv). Charged anolyte that has not dissociated from Li($^+$) is oxidized as Li-9a at +0.4 V (step v). The product of this oxidation rapidly dissociate to form Li($^+$) and 9a(•), which is consistent with the absence of a reductive couple at positive potentials.

To obtain values for the rates for association as well as the equilibrium constant for formation of Li-9a, the redox system proposed in Scheme 9 was computationally modeled. Diffusion constants for the anolyte were calculated to be on the order of $2\times10^{-9}$ m$^2$/s by analysis of changes in the potential at the first reductive couple with variable scan rates. This value was applied for all species in the simulation based on their similar molecular weights. A resistance of 400 ohms and no capacitance was simulated for all couples. With these parameters, the simulations were fit to experimental data acquired at variable scan rates (FIG. 9) in order to estimate the rate constants for association and dissociation of Li$^+$. The experimentally measured CVs features were accurately reproduced when the rate constant for Li$^+$ coordination was 10 M$^{-1}$s$^{-1}$ and the rate constant for dissociation was 0.5 s$^{-1}$. These rate constants indicate that the equilibrium constant for binding of Li$^+$ to 9a$^{(-)}$ is on the order of 20 M$^{-1}$.

Figure 9B:
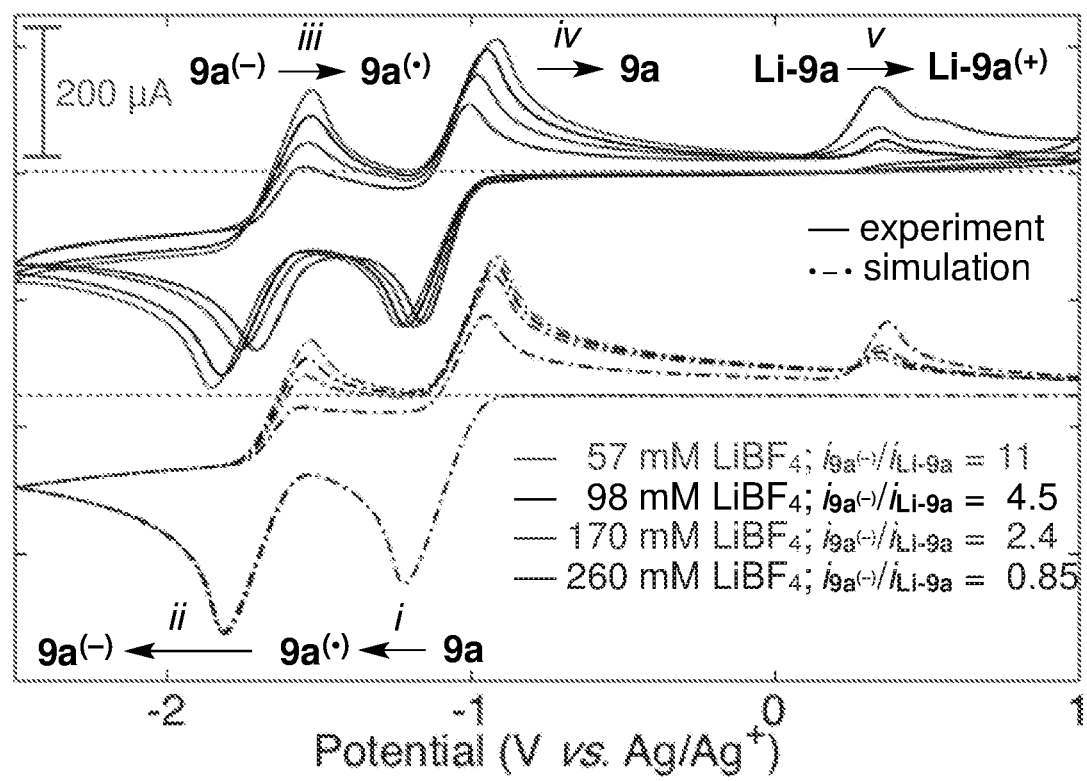
FIG. 9b is a graph showing cyclic voltammograms of 9a (0.01 M) in MeCN with varying concentrations of LiBF$_4$ at 200 mV/s scan rate (2nd cycles are plotted).

This system was further investigated at higher concentrations of Li$^+$. CVs were acquired at concentrations of LiBF$_4$ ranging from 57 mM to 260 mM with a constant 0.1 M concentration of 9a (FIG. 9b; solid lines). As expected, higher concentrations of LiBF$_4$ led to greater currents from the oxidation of Li-9a. The calculated rate constants (k$_f$=10 M$^{-1}$s$^{-1}$, k$^{-1}$=0.5 s$^{-1}$) were employed to model the effects of LiBF$_4$ concentration on the current peak-heights. The results are illustrated in FIG. 9b (dashed lines) and are in full agreement with the experimentally measured CVs.

Figure 10:
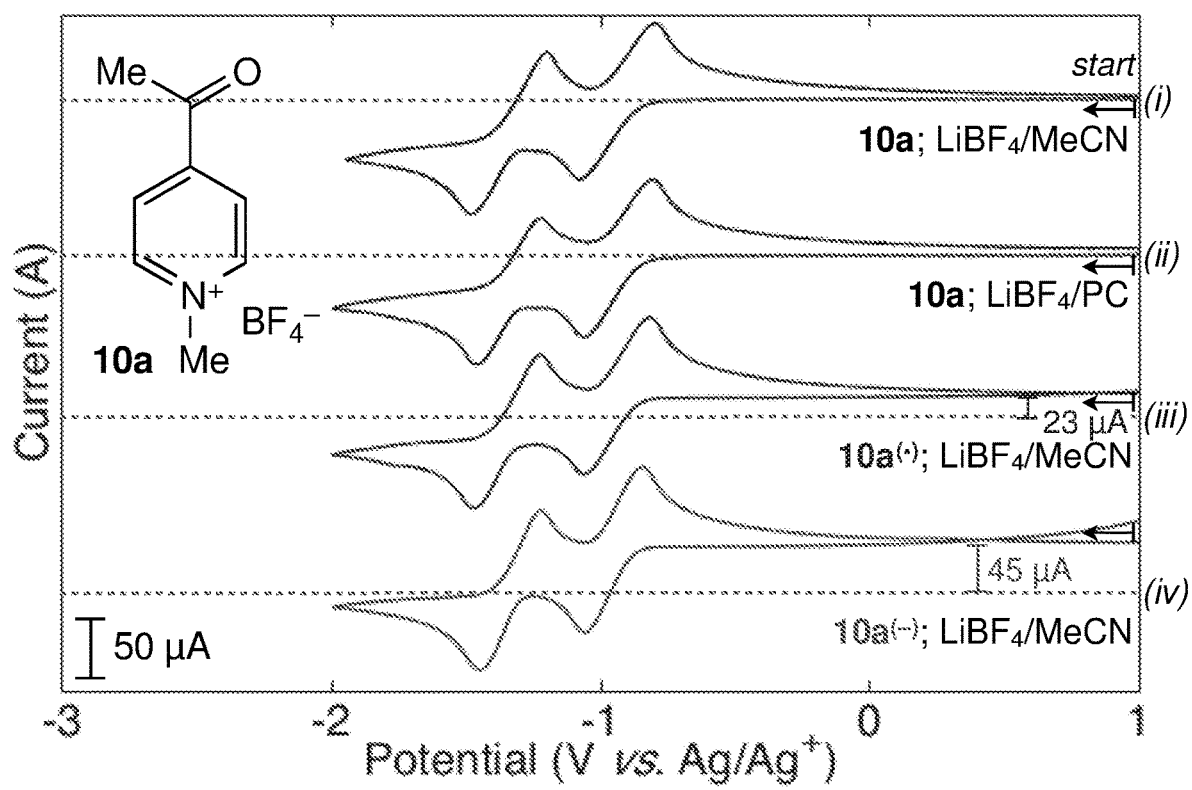
FIG. 10 is a graph showing cyclic voltammograms of 10a in MeCN (i) and PC (ii), and of 10a$^{(\cdot)}$ (iii) and 10a$^{(-)}$(iv) in MeCN. Conditions: 0.01 M 10a, 10a$^{(\cdot)}$, or 10a$^{(-)}$ with 0.1 M LiBF$_4$ in the specified solvent at 100 mV/s scan rate. 1st cycles are plotted. Gray dashed lines indicate the axis of origin. Arrows indicate start and direction of CV scan.

Example 7 Synthesis, Solubility, and Stability of Anolyte 10a and its Reduced Analogues 10a$^{(\cdot)}$ and 10a$^{(-)}$ Acetyl pyridinium salt 10a was prepared in 93% yield via methylation of 4-acetylpyridine with trimethyloxonium tetrafluoroborate. The CV of 10a in MeCN/LiBF$_4$ shows two reductive couples with peak height ratios close to 1 (FIG. 10, i). A direct comparison of 9a and 10a reveals that the first reductions occur at similar potentials (0.1 V difference) but that the second reduction of 10a is 0.4 V more positive than that of 9a. Notably, the CV of 10a in PC/LiBF$_4$ shows reversible couples at comparable potentials to those in MeCN/LiBF$_4$ (FIG. 10, ii). In contrast, the CV of 9a in PC/LiBF$_4$ is indicative of significant decomposition.

Figure 11:
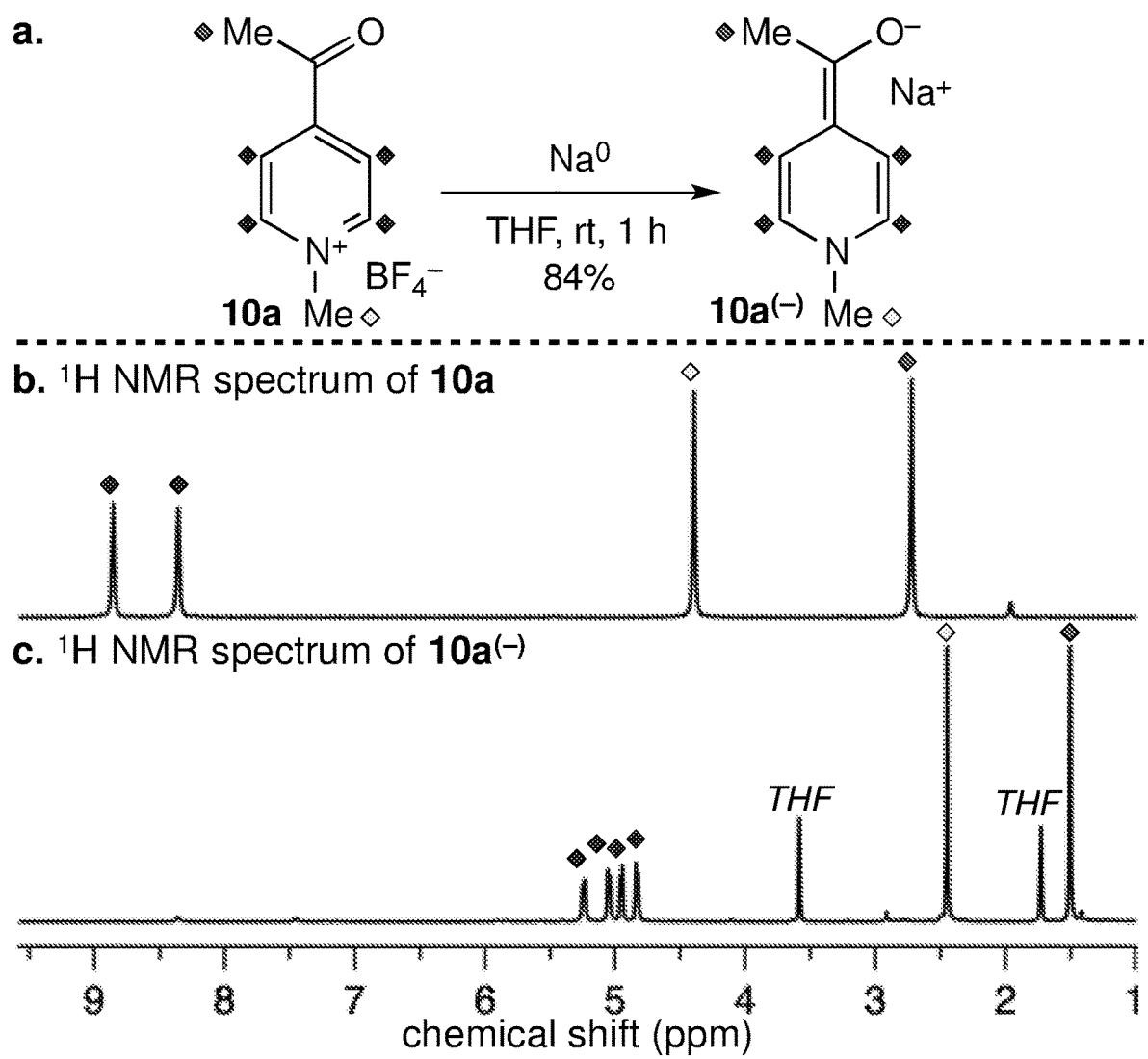

The materials generated during the reduction of 10a were independently synthesized. Compound Na-10a$^{(-)}$ was prepared via the 2e$^-$ reduction of 10a with sodium metal in THF. The product was isolated in 88% yield as an orange solid, and was characterized by elemental analysis, NMR spectroscopy, UV-vis spectroscopy, and CV. The $^1$H NMR resonances of Na-10a$^{(-)}$ are shifted upfield relative to those of 10a, consistent with a disruption of aromaticity (FIG. 11c vs. 11b). Furthermore, all four protons on the ring of Na-10a$^{(-)}$ are inequivalent. This is consistent with an enolate structure, in which the carbonyl is not freely rotating. The CV of Na-10a$^{(-)}$ in MeCN/LiBF$_4$ shows two couples at identical potentials to 10a (FIG. 10, iv). In addition, CVs measured at starting potentials of +1 V show baseline currents of 40-50 µA. This nonzero initial current is consistent with the presence of a pre-reduced material (Na-10a$^{(-)}$) that undergoes oxidation at high potentials. Importantly, no analogous current is observed at +1 V when the material is in its discharged state 10a (compare baseline currents relative to 0 µA lines in FIG. 10, i vs. iv). Unlike with Na-9a$^{(-)}$, the CV of Na-10a$^{(-)}$ does not change after standing in MeCN/LiBF$_4$ for 20 min at room temperature. This indicates that Na-10a$^{(-)}$ is stable under these conditions.

Figure 12:
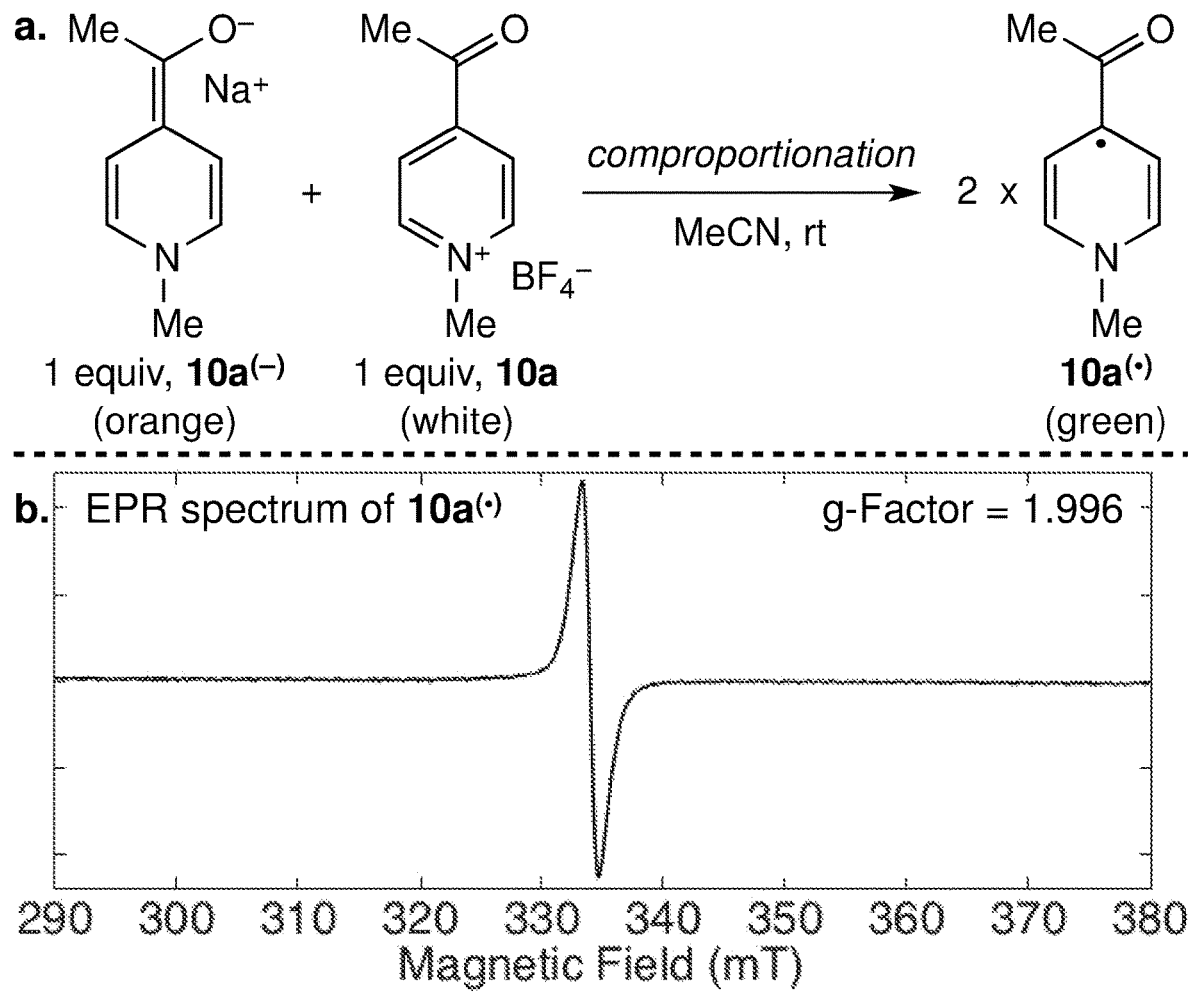
FIG. 12a is a scheme showing synthesis of 10a$^{(\cdot)}$ by comproportionation of 10a and Na-10a$^{(-)}$.
FIG. 12b is an EPR spectrum of a 1.0 mM solution of 10a$^{(\cdot)}$ in MeCN at 130 K.

The intermediate redox-state between the fully charged and discharged states of 10a, 10a$^{(\cdot)}$, was prepared according to a strategy involving comproportionation of 10a and Na-10a" (FIG. 12a). The dissolution of equimolar quantities of 10a (a white solid) and Na-10a$^{(-)}$ (an orange solid) in MeCN resulted in the instantaneous formation of a dark green solution. Dilution of this solution with diethyl ether led to the precipitation of NaBF$_4$. The solution was then collected, and the solvent was removed to afford 10a$^{(\cdot)}$ as a dark green solid in 91% yield.

The neutral radical 10a$^{(\cdot)}$ was characterized by elemental analysis, $^1$H NMR spectroscopy, EPR spectroscopy, UV-vis spectroscopy, and CV. As expected for a free radical, no resonances are observed in the $^1$H NMR spectrum of 10a$^{(\cdot)}$. The EPR spectrum of a frozen solution of 10a$^{(\cdot)}$ in MeCN shows a strong isotropic resonance (FIG. 12b). This signal is centered at 334 mT, and corresponds to a g-factor of 1.996. This value is consistent with a carbon centered radical, which generally has a g-factor near the value of a free electron (2.0036).

A comparison of the CV of 10a$^{(\cdot)}$ to those of 10a and Na-10a$^{(-)}$ shows two couples at identical potentials (FIG. 10, iii). Similar to Na-10a$^{(-)}$, a nonzero current is observed at the initial scanning potential of +1 V. This current (23 µA) is half of the initial current (45 µA) measured for Na-10a$^{(-)}$ at the same potentials (compare baselines of CVs in FIG. 10 iii vs. iv). At these initial potentials of +1 V, the reduced species Na-10a" undergoes two, 1e$^-$ oxidations, while 10a$^{(\cdot)}$ undergoes only one, 1e$^-$ oxidation. As such, these data are fully consistent with the different redox states of the molecule.

The solubilities of 10a, 10a$^{(\cdot)}$, and Na-10a$^{(-)}$ were determined by UV-vis spectroscopy in MeCN under an inert atmosphere. A solubility of 1.6±0.1 M in MeCN was measured for the parent compound 10a by analyzing the UV absorbance at 281 nm. This corresponds to 0.94 kg of a one-electron anolyte material per 1 kg of solvent, which exceeds the target of 0.8 kg anolyte per 1 kg solvent required to meet an RFB system price target of $120 per kWh. In addition to these solubility metrics, the low equivalent weight of 111 g/mol/e$^-$ for 10a is well below the target limit of 150 g/mol/e$^-$.

A saturated solution of 10a$^{(\cdot)}$ was prepared and analyzed at 322 nm by UV-vis spectroscopy. The saturation concentration of 10a$^{(\cdot)}$ was 5.4±0.5 M. An analogous study with Na-10a$^{(-)}$ (monitoring the absorbance at 426 nm) revealed a solubility of 0.062±0.007 M. The measured low solubility of Na-10a$^{(-)}$ is likely a reflection of the Na$^+$ counterion. Importantly, this is not the charge-balancing counterion that is obtained from electrochemical reduction in solutions with a LiBF$_4$ support. However, it is likely that the solubility of the doubly-reduced anolyte material will need further investigation prior to battery cycling studies at high concentration. Methods for electrochemical cycling of RFB materials with low solubility as well as the manipulation of solubility in MeCN are both well precedented.

Figure 13:
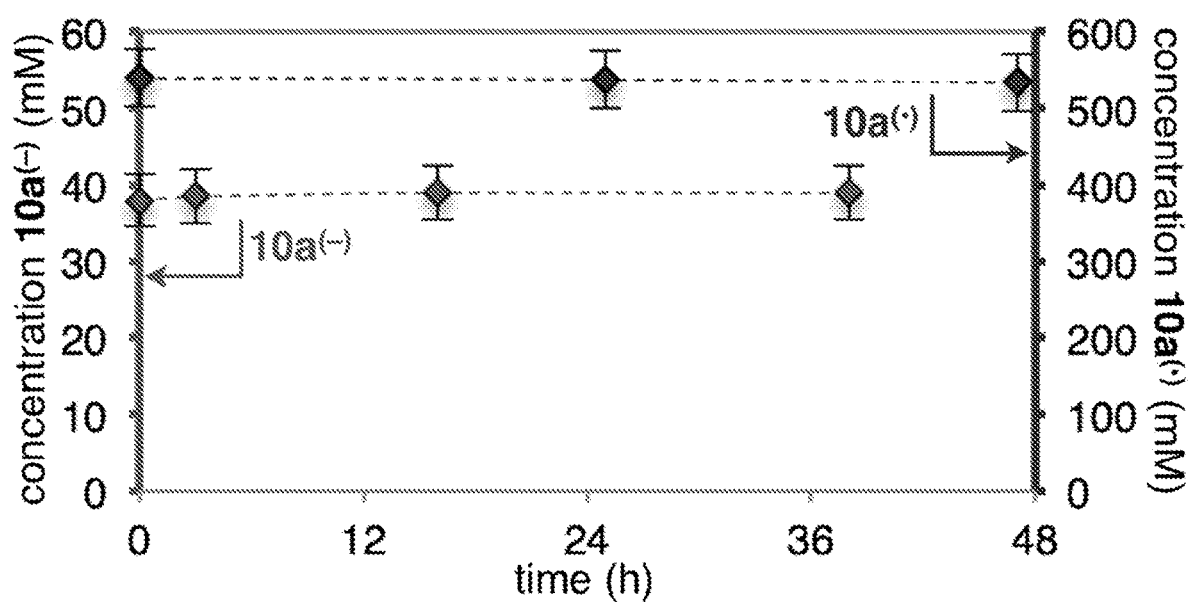
FIG. 13 is a graph of concentrations of 10a$^{(\cdot)}$ (540 mM initial concentration, blue) and Na-10a$^{(-)}$ (39 mM initial concentration, red) in MeCN measured by UV-vis over 36-48 h.

The stabilities of 10a, 10a$^{(\cdot)}$ and Na-10a$^{(-)}$ were monitored as solutions in MeCN by $^1$H NMR spectroscopy or UV-vis spectroscopy. Separate solutions of 10a, 10a$^{(\cdot)}$ and Na-10a$^{(-)}$ in MeCN were prepared at 480 mM, 540 mM and 39 mM concentrations, respectively. The parent compound 10a was monitored by $^1$H NMR spectroscopy against an internal standard of 1,3,5-trimethoxybenzene. No measurable decomposition was detected over four days even in the presence of air and moisture. Solutions of the reduced species 10a$^{(\cdot)}$ and Na-10a$^{(-)}$ were stored at room temperature under nitrogen, and the concentrations of the solutions were measured periodically over 36 h or 48 h by UV-vis spectroscopy (FIG. 13). During this period, the concentrations of the reduced anolytes did not change, suggesting that these materials are also stable and amenable to storage for days in solution.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. An anolyte solution for a redox flow battery comprising a non-aqueous solvent; a supporting electrolyte; and a compound of formula I as an anolyte material:

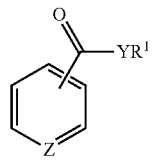
(I)

wherein
Y is selected from the group consisting of null, O, and NR$^3$;
Z is selected from the group consisting of N$^+$O and N$^+$R$^-$;
R$^1$ is selected from the group consisting of optionally substituted C$_{1-10}$ alkyl, C$_{3-12}$ cycloalkyl, and optionally substituted phenyl;
R$^3$ is an optionally substituted C$_{1-10}$ alkyl; and
R is a Lewis acid.

2. An anolyte solution for a redox flow battery comprising a non-aqueous solvent; a supporting electrolyte; and a compound of formula III as an anolyte material:

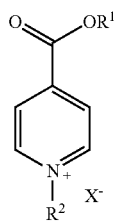
(III)

wherein
R$^1$ is selected from the group consisting of optionally substituted C$_{1-10}$ alkyl, C$_{3-12}$ cycloalkyl, and optionally substituted phenyl;
R$^2$ is selected from the group consisting of methyl, ethyl, propyl, butyl, and adamantyl; and
X$^-$ is an anion.

3. The anolyte solution of claim 1, wherein R$^1$ is selected from the group consisting of methyl, ethyl, propyl, butyl, adamantyl, and CF$_3$.

4. The anolyte solution of claim 1, wherein R is selected from the group consisting of boron trihalides, trialkyl boranes, aluminium(III) trihalides, aluminium(III) alkoxides, and phosphorus pentahalides.

5. The anolyte solution of claim 1, wherein R is selected from the group consisting of BF$_3$, BCl$_3$, AlCl$_3$, AlBr$_3$, and Al(O$^i$Pr)$_3$.

6. The anolyte solution of claim 2, wherein X$^-$ is selected from the group consisting of I$^-$, Br$^-$, Cl$^-$, F$^-$, PF$_6^-$, BF$_4^-$, $^-$OAc, SO$_4^{2-}$, ClO$_4^-$, NO$_3^-$, alkoxides such as $^-$OMe, CF$_3$SO$_3^-$, CH$_3$C$_6$H$_4$SO$_3^-$, SbF$_6^-$, SCN$^-$, N$_3^-$, CN$^-$, and BPh$_4^-$.

7. The anolyte solution of claim 1, wherein the compound of formula I is selected from the group consisting of:

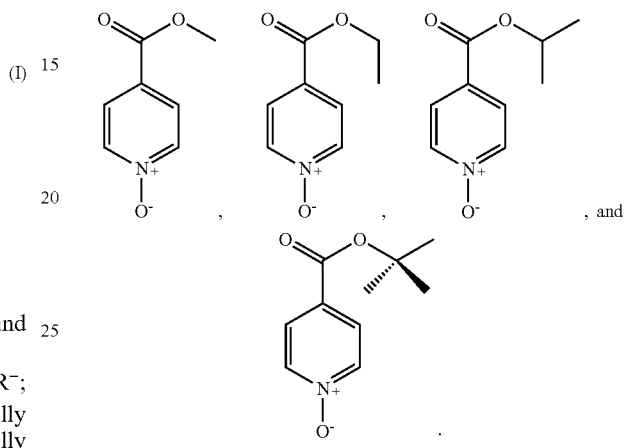

8. The anolyte solution of claim 1, wherein the compound of formula I is selected from the group consisting of:

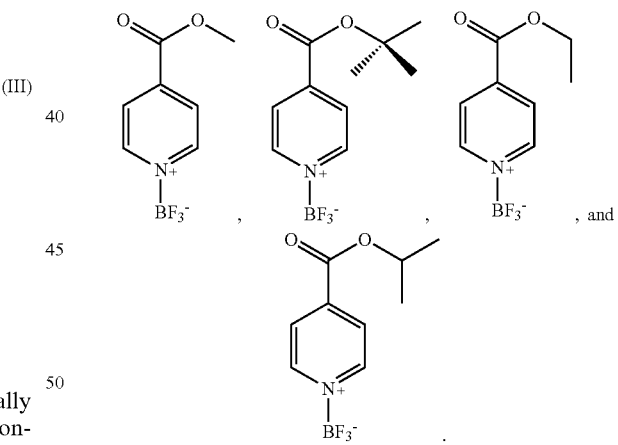

9. The anolyte solution of claim 2, wherein the compound of formula III is selected from the group consisting of:

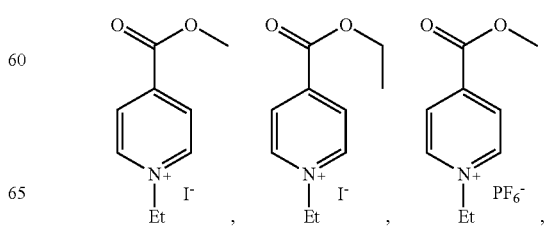

-continued

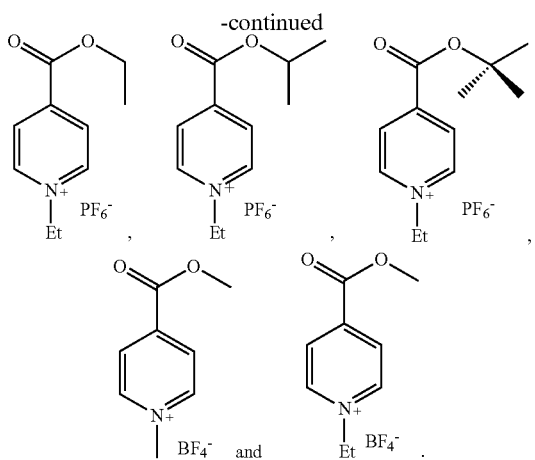

10. An anolyte solution for a redox flow battery comprising a non-aqueous solvent; a supporting electrolyte; and compound 10a as an anolyte material:

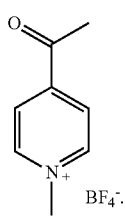

(10a)

11. The anolyte solution of claim 1, wherein the non-aqueous solvent is selected from the group consisting of acetonitrile, acetone, dimethylacetamide, diethyl carbonate, 1,4-dioxane, 1,2-dimethoxy ethane, dichloromethane, 1,2-dichloroethane, nitrobenzene, nitromethane, dimethyl carbonate, dimethyl formamide, 2-methyltetrahydrofuran, tetrahydrofuran, 2,4-dimethyltetrahydrofuran, methoxybenzene, diglyme, y-butyrolactone, propylene carbonate, ethylene carbonate, N-methyl-2-pyrrolidone, 4-methyl-2-pentanone, acetylacetone, proprionitrile, butryonitrile, isobutyronitrile, benzonitrile, dimethylsulfoxide, sulfolane, dimethylthioformamide, methyl acetate, ethyl acetate, fluoroethylene carbonate, and N,N-dimethylacetamide.

12. The anolyte solution of claim 1, wherein the supporting electrolyte comprises $Li^+$.

13. A redox flow battery comprising the anolyte solution of claim 1 and further comprising a cathode cell comprising a cathode and a catholyte solution; an anode cell comprising an anode and the anolyte solution; and an ion exchange membrane disposed between the cathode cell and the anode cell.

14. The anolyte solution of claim 2, wherein the non-aqueous solvent is selected from the group consisting of acetonitrile, acetone, dimethylacetamide, diethyl carbonate, 1,4-dioxane, 1,2-dimethoxy ethane, dichloromethane, 1,2-dichloroethane, nitrobenzene, nitromethane, dimethyl carbonate, dimethyl formamide, 2-methyltetrahydrofuran, tetrahydrofuran, 2,4-dimethyltetrahydrofuran, methoxybenzene, diglyme, y-butyrolactone, propylene carbonate, ethylene carbonate, N-methyl-2-pyrrolidone, 4-methyl-2-pentanone, acetylacetone, proprionitrile, butryonitrile, isobutyronitrile, benzonitrile, dimethylsulfoxide, sulfolane, dimethylthioformamide, methyl acetate, ethyl acetate, fluoroethylene carbonate, and N,N-dimethylacetamide.

15. The anolyte solution of claim 10, wherein the non-aqueous solvent is selected from the group consisting of acetonitrile, acetone, dimethylacetamide, diethyl carbonate, 1,4-dioxane, 1,2-dimethoxy ethane, dichloromethane, 1,2-dichloroethane, nitrobenzene, nitromethane, dimethyl carbonate, dimethyl formamide, 2-methyltetrahydrofuran, tetrahydrofuran, 2,4-dimethyltetrahydrofuran, methoxybenzene, diglyme, y-butyrolactone, propylene carbonate, ethylene carbonate, N-methyl-2-pyrrolidone, 4-methyl-2-pentanone, acetylacetone, proprionitrile, butryonitrile, isobutyronitrile, benzonitrile, dimethylsulfoxide, sulfolane, dimethylthioformamide, methyl acetate, ethyl acetate, fluoroethylene carbonate, and N,N-dimethylacetamide.

16. The anolyte solution of claim 2, wherein the supporting electrolyte comprises $Li^+$.

17. The anolyte solution of claim 10, wherein the supporting electrolyte comprises $Li^+$.

18. A redox flow battery comprising the anolyte solution of claim 2 and further comprising a cathode cell comprising a cathode and a catholyte solution; an anode cell comprising an anode and the anolyte solution; and an ion exchange membrane disposed between the cathode cell and the anode cell.

19. A redox flow battery comprising the anolyte solution of claim 10 and further comprising a cathode cell comprising a cathode and a catholyte solution; an anode cell comprising an anode and the anolyte solution; and an ion exchange membrane disposed between the cathode cell and the anode cell.

* * * * *